(12) United States Patent
Buechler et al.

(10) Patent No.: US 7,341,838 B2
(45) Date of Patent: Mar. 11, 2008

(54) POLYPEPTIDES RELATED TO NATRIURETIC PEPTIDES AND METHODS OF THEIR IDENTIFICATION AND USE

(75) Inventors: Kenneth F. Buechler, San Diego, CA (US); Eric Thomas Fung, Mountain View, CA (US); Tai-Tung Yip, Cupertino, CA (US)

(73) Assignees: Biosite Incorporated, San Diego, CA (US); Vermillion, Inc., Wilmington, DE (US)

( * ) Notice: Subject to any disclaimer, the term of this patent is extended or adjusted under 35 U.S.C. 154(b) by 369 days.

(21) Appl. No.: 10/827,919

(22) Filed: Apr. 19, 2004

(65) Prior Publication Data

US 2005/0064511 A1    Mar. 24, 2005

Related U.S. Application Data

(63) Continuation-in-part of application No. 10/419,059, filed on Apr. 17, 2003.

(60) Provisional application No. 60/466,358, filed on Apr. 28, 2003.

(51) Int. Cl.
*G01N 33/53* (2006.01)
(52) U.S. Cl. ..................................... 435/7.1
(58) Field of Classification Search ................. 435/7.1; 436/514, 15, 8; 930/10
See application file for complete search history.

(56) References Cited

U.S. PATENT DOCUMENTS

| | | | |
|---|---|---|---|
| 5,352,587 A | 10/1994 | Chang et al. | |
| 5,422,393 A | 6/1995 | Bricker et al. | |
| 5,786,163 A | 7/1998 | Hall | |
| 6,117,644 A | 9/2000 | Debold | |
| 6,124,430 A | 9/2000 | Mischak et al. | |
| 6,756,483 B1 | 6/2004 | Bergmann et al. | |
| 2002/0055186 A1 | 5/2002 | Barry et al. | |
| 2003/0219734 A1 | 11/2003 | Buechler | |
| 2004/0171064 A1 | 9/2004 | Dahlen et al. | |

FOREIGN PATENT DOCUMENTS

| | | |
|---|---|---|
| EP | 1 666 881 A2 | 6/2006 |
| EP | 1666881 A2 | 6/2006 |
| WO | WO 02/23191 A1 | 3/2002 |
| WO | WO 2004/094459 A2 | 11/2004 |

OTHER PUBLICATIONS

Bidzseranova et al., "Structure-activity Studies on the Effects of Atrial Natriuretic Peptide, Brain Natriuretic Peptide and Their Analogs on Fear-motivated Learning Behavior in Rats," *Neuropeptides*, 23:61-65 (1992).
Norman et al., "Degradation of Brain natriuretic Peptide By Neutral Endopeptidase: Species Specific Sites of Proteolysis Determined by Mass Spectrometry," *Biochemical and Biophysical Res. Comm.*, 175(1):22-30 (1991).
Venugopal, J., "cardiac natriuretic peptides—hope or hype?," *J. Clkin. Pharmacy and Therapeutics*,26:15-31 (2001).
U.S. Appl. No. 60/466,358, filed Apr. 28, 2003, Yip, T-T.

*Primary Examiner*—Ann Y. Lam
(74) *Attorney, Agent, or Firm*—Townsend and Townsend and Crew LLP

(57) ABSTRACT

The present invention relates to the identification and use of polypeptides that bind to antibodies directed to a desired polypeptide of interest. Using natriuretic peptides and their precursors, and in particular BNP, as an example, the present invention describes a number of natriuretic peptides fragments produced in biological samples, most preferably blood-derived samples, that bind to antibodies directed to BNP. Because production of such fragments is an ongoing process that may be a function of, inter alia, the elapsed time between onset of an event triggering natriuretic peptide release into the tissues and the time the sample is obtained or analyzed; the elapsed time between sample acquisition and the time the sample is analyzed; the type of tissue sample at issue; the storage conditions; the quantity of proteolytic enzymes present; etc., such fragments may be used when both designing an assay for one or more natriuretic peptides, and when performing such an assay, in order to provide an accurate prognostic or diagnostic result.

45 Claims, 15 Drawing Sheets

B-type Natriuretic Peptide (BNP) Precursor

His-Pro-Leu-Gly-Ser-Pro-Gly-Ser-Ala-Ser-Asp-Leu-Glu-Thr-Ser-Gly-Leu-Gln-Glu-Gln-Arg-Asn-His-Leu-Gln-Gly-Lys-Leu-Ser-Glu-Leu-Gln-Val-Glu-Gln-Thr-Ser-Leu-Glu-Pro-Leu-Gln-Glu-Ser-Pro-Arg-Pro-Thr-Gly-Val-Trp-Lys-Ser-Arg-Glu-Val-Ala-Thr-Glu-Gly-Ile-Arg-Gly-His-Arg-Lys-Met-Val-Leu-Tyr-Thr-Leu-Arg-Ala-Pro-Arg-Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys-Lys-Val-Leu-Arg-Arg-His- 108

| | | | |
|---|---|---|---|
| 1-108 | | 11903.6 Da | pI 10.6 |
| 77-108 | BNP-32 | 3464.1 Da | pI 11.4 |
| 1-21 | | 2166.3 Da | pI 4.5 |

FIG. 1

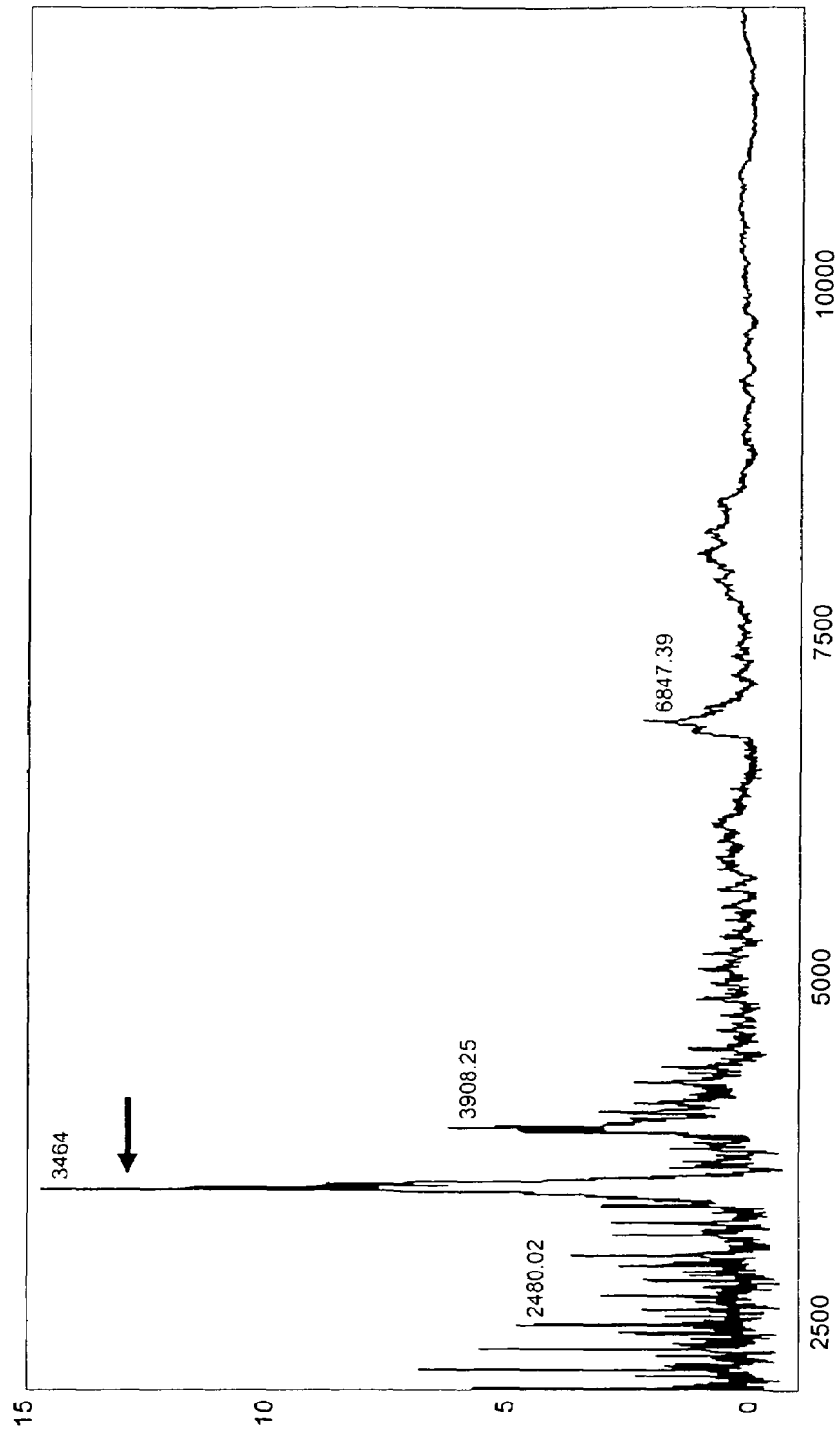

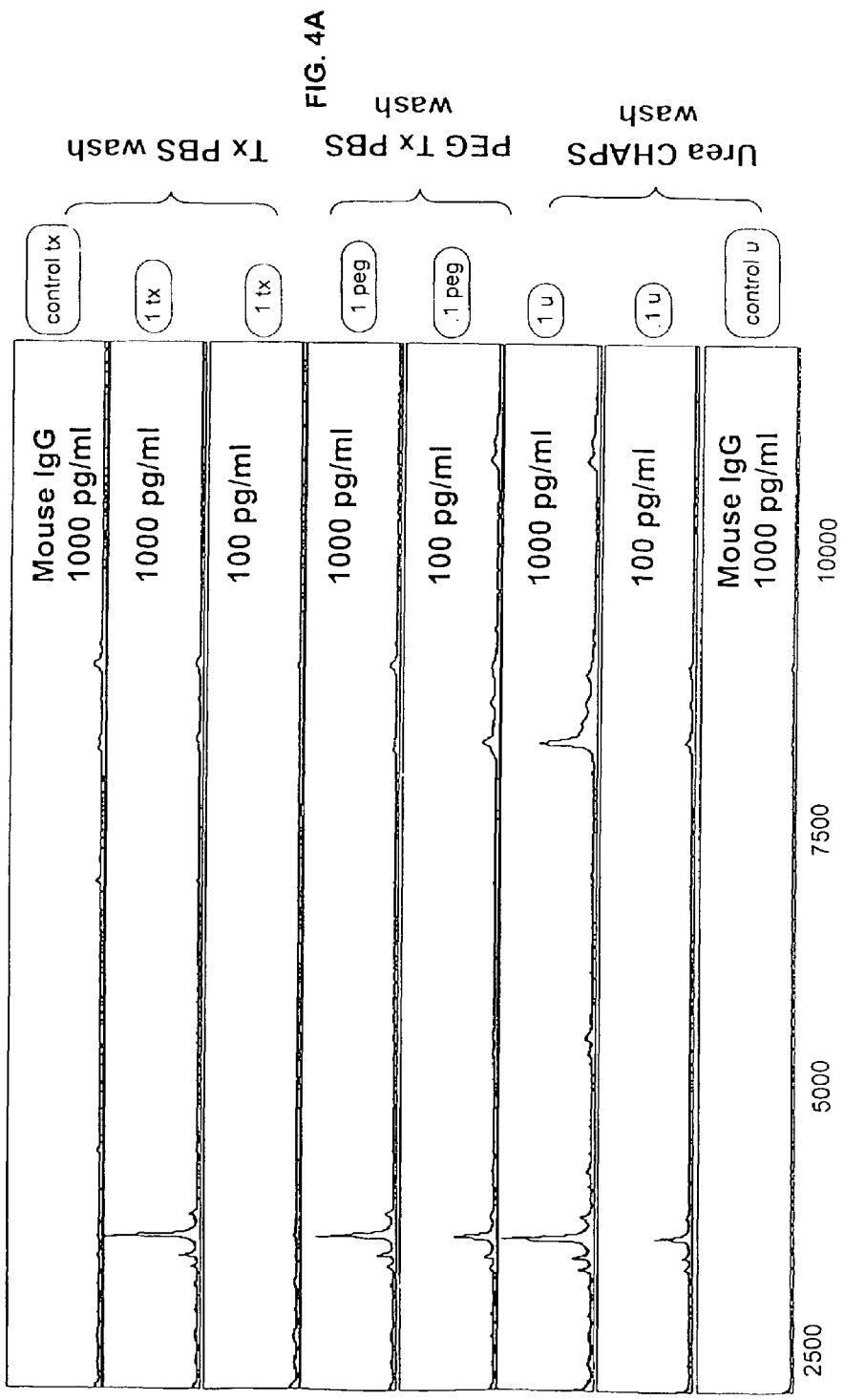

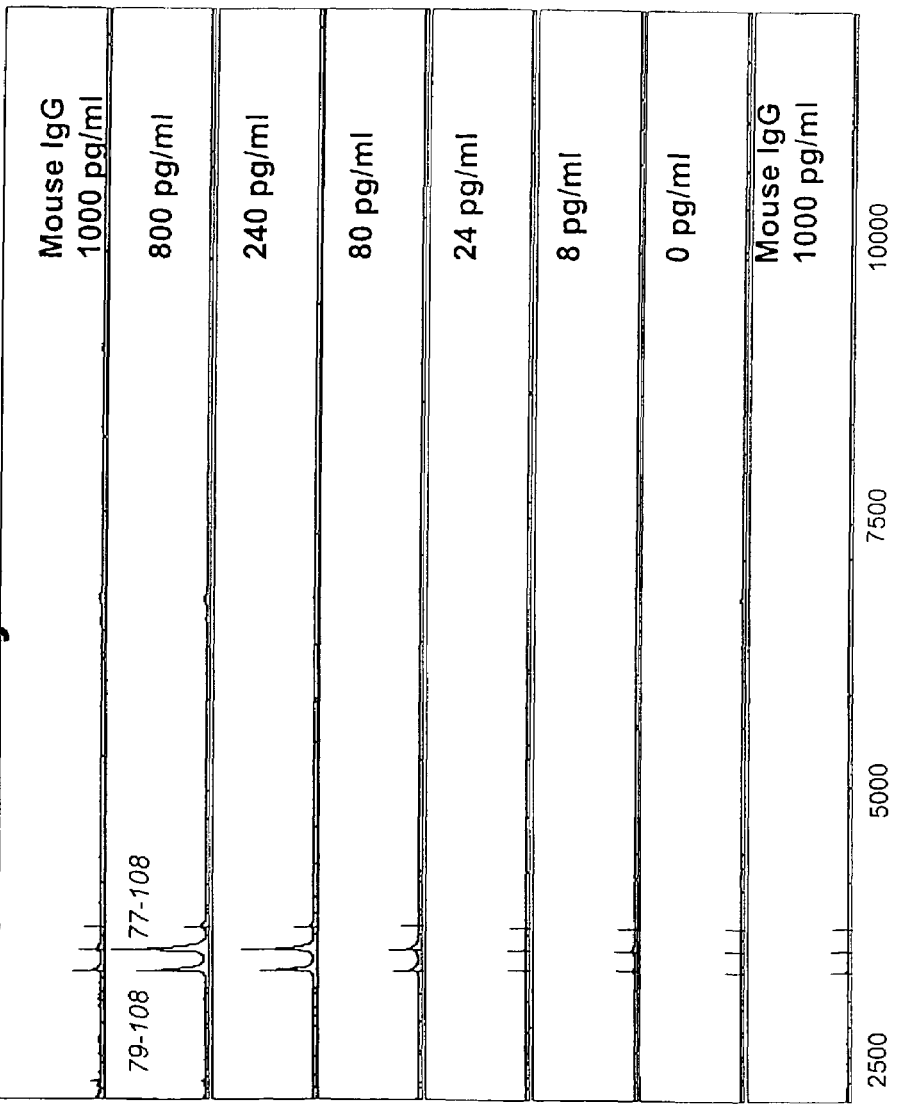

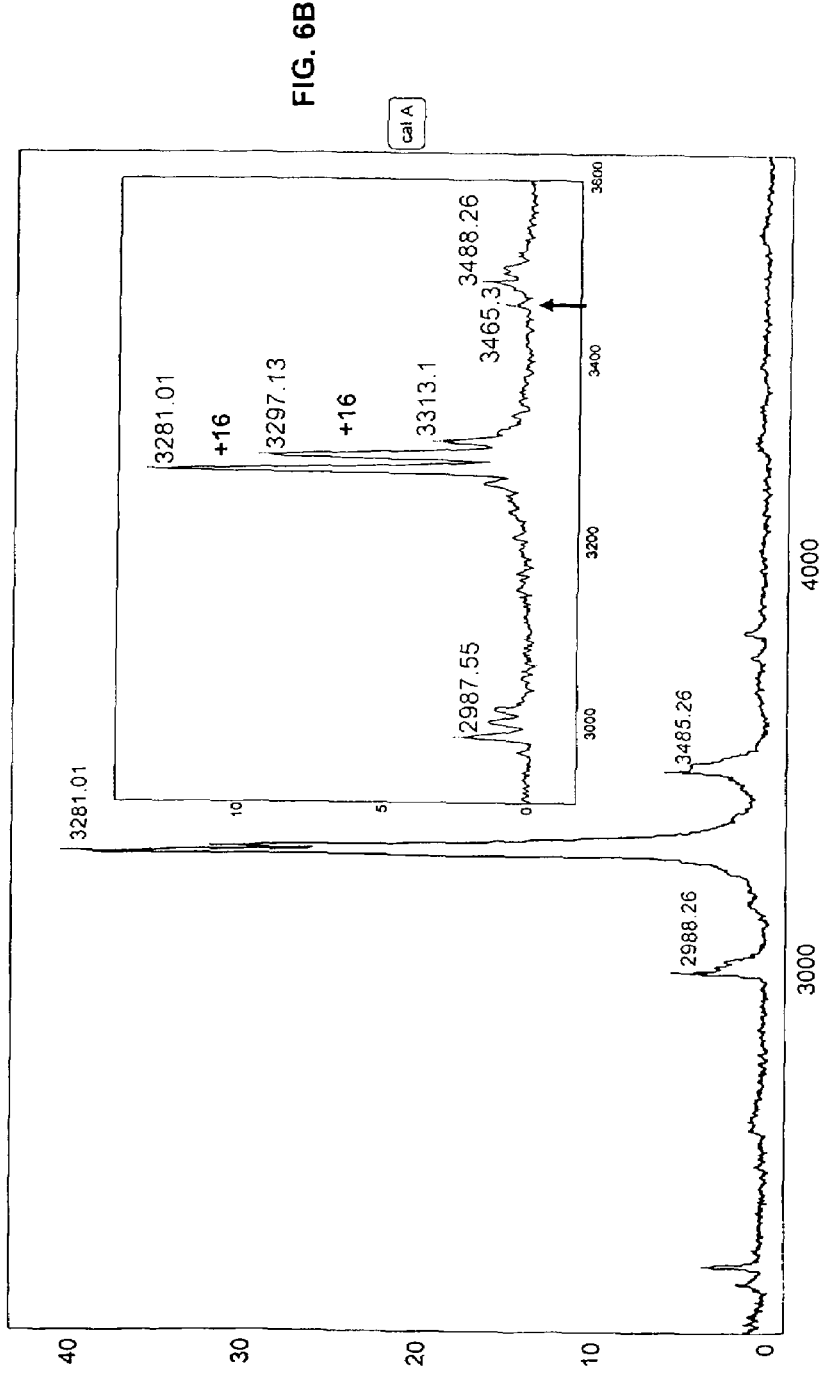

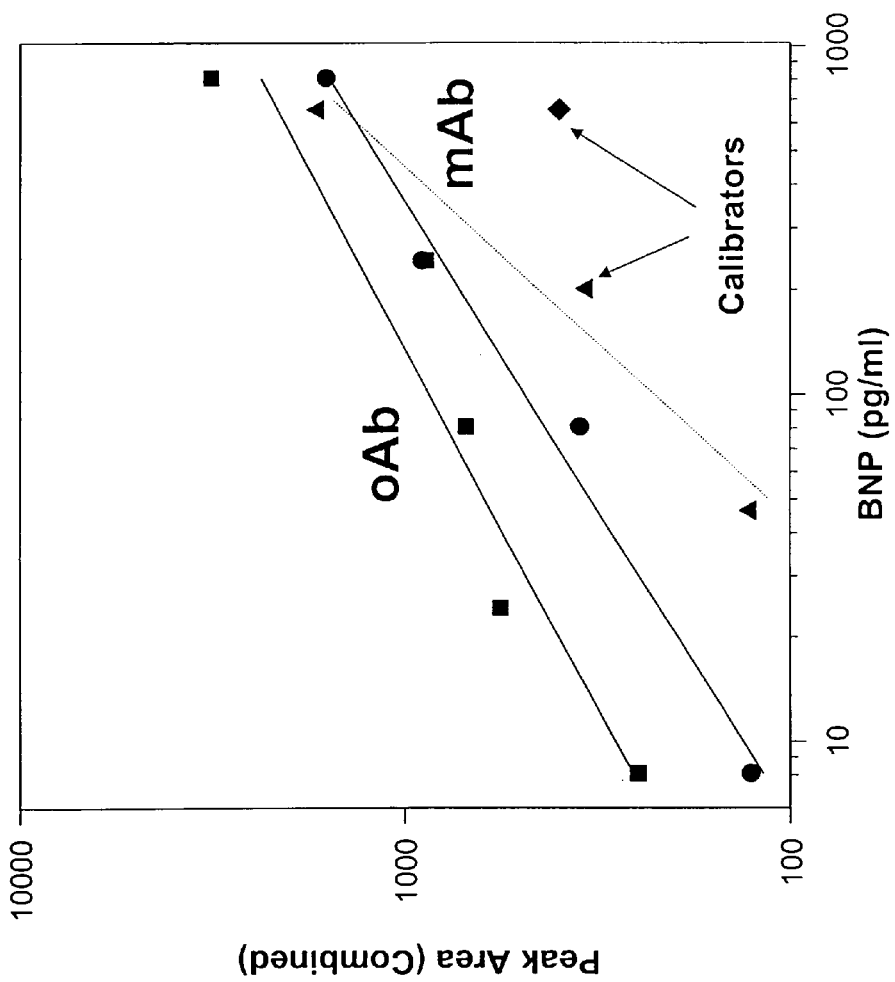

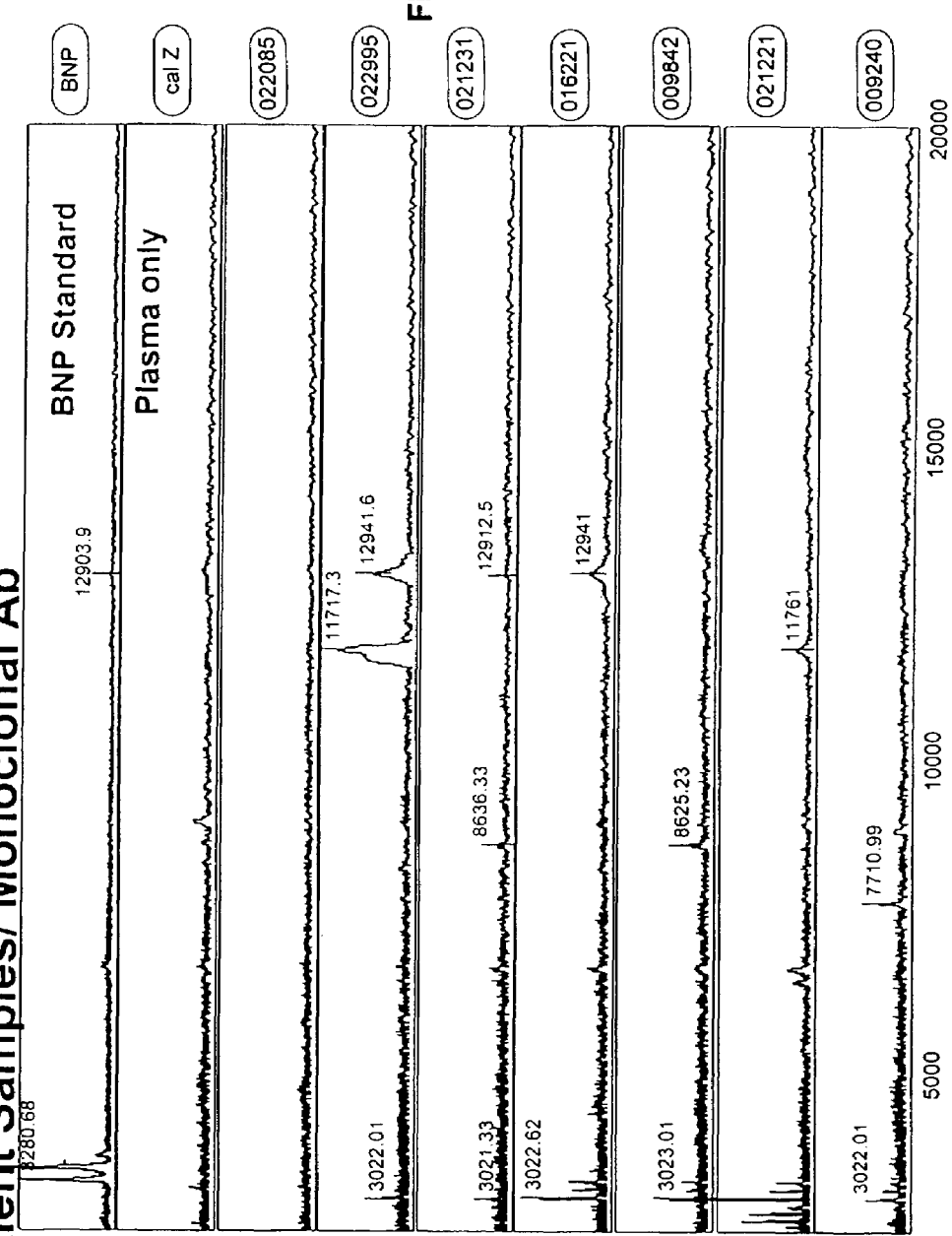

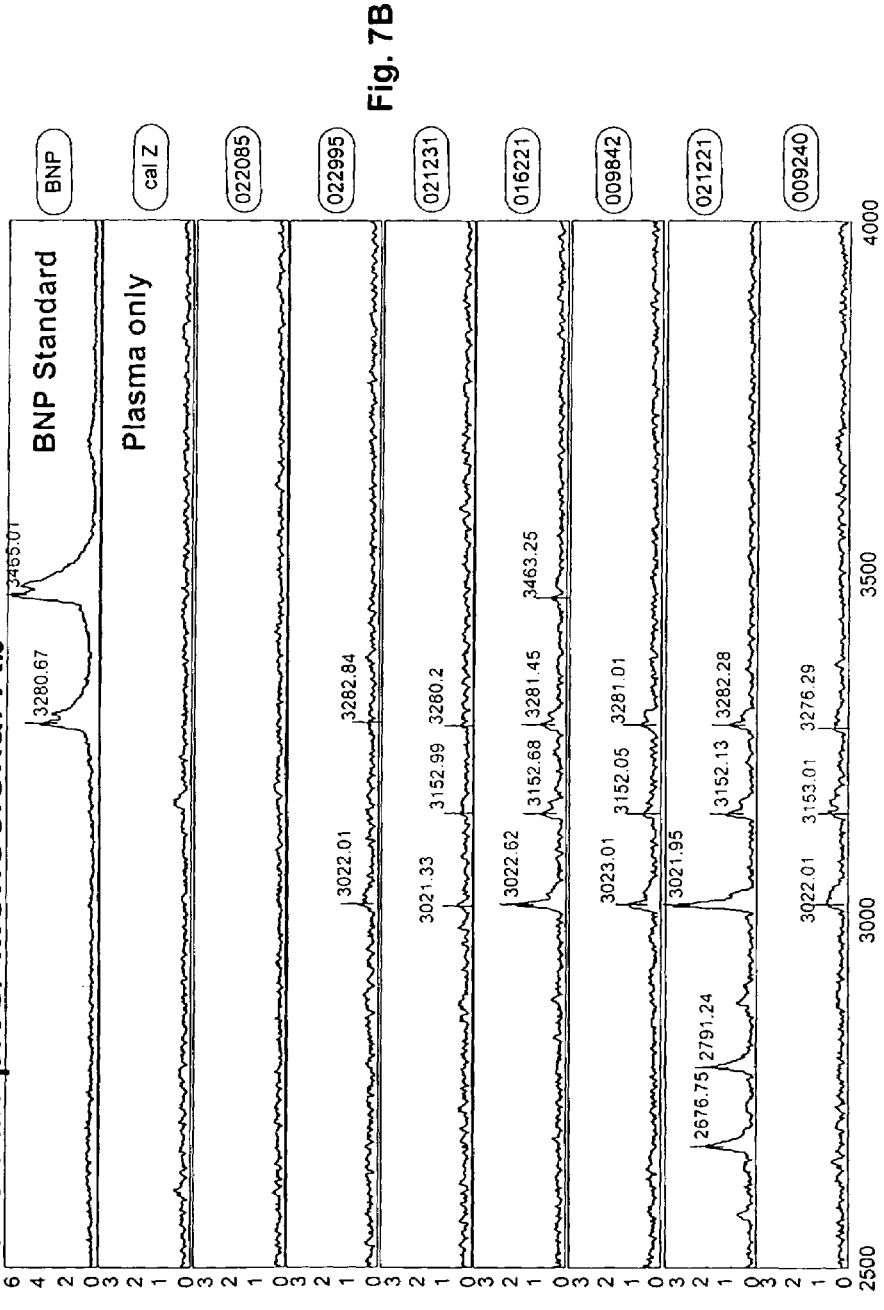

POLYPEPTIDES RELATED TO NATRIURETIC PEPTIDES AND METHODS OF THEIR IDENTIFICATION AND USE

CROSS-REFERENCE TO RELATED APPLICATIONS

The present application is a continuation-in-part of U.S. Ser. No. 10/419,059 filed Apr. 17, 2003, incorporated by reference in its entirety for all purposes. The present application also is a nonprovisional of and claims the benefit of provisional application 60/466,358 filed Apr. 28, 2003, incorporated by reference in its entirety for all purposes.

FIELD OF THE INVENTION

The present invention relates to the identification and use of polypeptides that are derived from biological active peptides, the peptides generated when the biological peptide is generated and the precursors of the aforementioned peptides.

BACKGROUND OF THE INVENTION

The following discussion of the background of the invention is merely provided to aid the reader in understanding the invention and is not admitted to describe or constitute prior art to the present invention.

Natriuretic peptides are a group of naturally occurring substances that act in the body to oppose the activity of the renin-angiotensin system. There are three major natriuretic peptides: atrial natriuretic peptide (ANP), which is synthesized in the atria; brain-type natriuretic peptide (BNP), which is synthesized in the ventricles; and C-type natriuretic peptide (CNP), which is synthesized in the brain.

Mature A-type natriuretic peptide (ANP) (also referred to as atrial natriuretic peptide) is a 28 amino acid peptide that is synthesized, stored, and released by atrial myocytes in response to atrial distension, angiotensin II stimulation, endothelin, and sympathetic stimulation (beta-adrenoceptor mediated). Mature ANP is synthesized as a precursor molecule (pro-ANP) that is converted to an active form by proteolytic cleavage. In addition to atrial natriuretic peptide (ANP99-126) itself, linear peptide fragments from its N-terminal prohormone segment have also been reported to have biological activity.

Mature B-type natriuretic peptide (BNP) (also called brain-type natriuretic peptide) is a 32 amino acid, 4 kDa peptide that is involved in the natriuresis system to regulate blood pressure and fluid balance (Bonow, R. O., *Circulation* 93:1946-1950, 1996). The precursor to BNP is synthesized as a 108-amino acid molecule, referred to herein as "pro-BNP" that is proteolytically processed into a 76-amino acid N-terminal peptide (amino acids 1-76), referred to as "NT pro BNP" and the 32-amino acid mature hormone, referred to as BNP or BNP32 (amino acids 77-108). It has been suggested that each of these species—NT pro-BNP, BNP-32, and the pre-pro-BNP—can circulate in human plasma (Tateyama et al., *Biochem. Biophys. Res. Commun.* 185:760-7, 1992; Hunt et al., *Biochem. Biophys. Res. Commun.* 214:1175-83, 1995).

Mature C-type natriuretic peptide (CNP) a 22-amino acid peptide that is the primary active natriuretic peptide in the human brain; CNP is also considered to be an endothelium-derived relaxant factor, which acts in the same way as nitric oxide (NO) (Davidson et al., *Circulation* 93:1155-9, 1996). CNP is structurally related to A-type natriuretic peptide (ANP) and B-type natriuretic peptide (BNP); however, while ANP and BNP are synthesized predominantly in the myocardium, CNP is synthesized in the vascular endothelium as a precursor (pro-CNP) (Prickett et al., *Biochem. Biophys. Res. Commun.* 286:513-7, 2001). CNP is thought to possess vasodilator effects on both arteries and veins and has been reported to act mainly on the vein by increasing the intracellular cGMP concentration in vascular smooth muscle cells.

ANP and BNP are released in response to atrial and ventricular stretch, respectively, and will cause vasorelaxation, inhibition of aldosterone secretion in the adrenal cortex, and inhibition of renin secretion in the kidney. Both ANP and BNP will cause natriuresis and a reduction in intravascular volume, effects amplified by the antagonism of antidiuretic hormone (ADH). The physiologic effects of CNP differ from those of ANP and BNP; CNP has a hypotensive effect, but no significant diuretic or natriuretic actions. Increased blood levels of natriuretic peptides have been found in certain disease states, suggesting a role in the pathophysiology of those diseases, including stroke, congestive heart failure (CHF), cardiac ischemia, systemic hypertension, and acute myocardial infarction. See, e.g., WO 02/089657; WO 02/083913; and WO 03/016910, each of which is hereby incorporated in its entirety, including all tables, figures, and claims.

The natriuretic peptides, alone, collectively, and/or together with additional proteins, can also serve as disease markers and indicators of prognosis in various cardiovascular conditions. For example, BNP, which is synthesized in the cardiac ventricles and correlates with left ventricular pressure, amount of dyspnea, and the state of neurohormonal modulation, makes this peptide the first potential marker for heart failure. Measurement of plasma BNP concentration is evolving as a very efficient and cost effective mass screening technique for identifying patients with various cardiac abnormalities regardless of etiology and degree of LV systolic dysfunction that can potentially develop into obvious heart failure and carry a high risk of a cardiovascular event. Finding a simple blood test that would aid in the diagnosis and management of patients with CHF clearly would have a favorable impact on the staggering costs associated with the disease.

Removal of the natriuretic peptides from the circulation is affected mainly by binding to clearance receptors and enzymatic degradation in the circulation. See, e.g., Cho et al., *Heart Dis.* 1: 305-28, 1999; Smith et al., *J. Endocrinol.* 167: 239-46, 2000. Additionally, human pro-BNP is reported to be processed in serum such that circulating pre-pro-BNP is unlikely to be the intact 108 amino acid form. Hunt et al., *Peptides* 18: 1475-81, 1997. But some confusion over the stability of the natriuretic peptides, particularly in blood-derived samples (e.g., serum, plasma, whole blood) has been reported. For example, while Norman et al. (*Biochem. Biophys. Res. Commun.* 28: 175: 22-30, 1991) report that neutral endopeptidase can cleave human BNP between residues 2 and 3, between residues 4 and 5, and between residues 17 and 18, Smith et al. (*J. Endocrinol.* 167: 239-46, 2000) report that human BNP is not significantly degraded by purified neutral endopeptidase. Similarly, Shimizu et al. (*Clin. Chem. Acta* 305: 181-6, 2001), Gobinet-Georges et al. (*Clin. Chem. Lab. Med.* 38: 519-23, 2000) and Murdoch et al. (*Heart* 78: 594-7, 1997) report that BNP is stable in certain blood-derived samples or when blood is collected under certain conditions. A more recent report by Shimizu et al. (*Clin. Chem. Acta* 316: 129-35, 2002) indicates that 94% of BNP in whole blood was a digested form in which 2 amino terminal residues had been removed; and that BNP in plasma was degraded to a number of unidentified forms.

SUMMARY OF THE INVENTION

The invention provides a purified BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. Optionally, one or more methionine residues of the fragment are oxidized.

In various embodiments, the present invention relates to any purified, and preferably substantially purified, BNP polypeptide(s) other than pre-pro-BNP, BNP1-108, BNP1-76, and BNP77-108. In preferred embodiments, the present invention relates to one or more substantially purified BNP polypeptides selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. Optionally, BNP80-108, BNP30-106, BNP86-108, BNP77-107, BNP77-106, BNP77-103, BNP1-13, and BNP62-76 are excluded in their individually purified forms.

The present invention also relates to one or more purified, and preferably substantially purified, natriuretic peptide fragments other than mature ANP, BNP, and CNP, their precursor molecules, and the fragments generated by cleavage of the precursor molecules into the mature ANP, BNP, and CNP peptides.

The invention further provides a method of assaying BNP. The method entails capturing one or more BNP polypeptides from a subject sample; and specifically measuring a presence or an amount of at least one captured BNP polypeptide selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. Preferred BNP polypeptides include BNP77-106, BNP39-86, BNP53-85, BNP66-98, BNP30-106, BNP11-107, BNP9-106, BNP69-100, and BNP76-107. Optionally, the one or more BNP polypeptides are from a clinical sample, and the method further comprising correlating the presence or amount of at least one captured BNP polypeptide with a clinical parameter. Optionally, the method further comprises specifically measuring at least one BNP polypeptide selected from the group consisting of BNP1-76, BNP77-108, BNP1-108 and pre-proBNP and correlating the measurement(s) with the clinical parameter. Optionally, the specific measuring step is performed by mass spectrometry. Optionally, the capturing step comprises providing a SELDI probe comprising an antibody attached to a surface of a support; contacting the antibody with a sample, whereby the antibody captures the BNP polypeptides from the sample; and the specifically measuring step comprises specifically measuring the presence or amount of the at least one captured BNP polypeptide by SELDI. Optionally, the capturing captures a plurality of BNP polypeptides selected from the group and the specifically measuring specifically measures a plurality of BNP polypeptides selected from the group.

The invention further provides a method of classifying the pathology of a test sample. The method entails specifically measuring the presence or amount of one or more BNP polypeptides selected from each of a plurality of samples of a first class characterized by a BNP-related pathology. A presence or amount of said one or more BNP polypeptides from a plurality of samples of a second class is specifically measured, wherein the second class is characterized by absence of a BNP-related pathology. A classification model based on the measurements that classifies a test sample into the first class or the second class. At least one of the BNP polypeptides is selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106.

The invention further comprises a method for specifically measuring pre-pro-BNP, BNP1-76, BNP77-108, or BNP1-108 in a sample containing at least one other BNP polypeptide. The method entails capturing BNP polypeptides from a sample, wherein the polypeptides comprise at least one BNP polypeptide selected from a first group consisting of BNP1-76, BNP77-108, BNP1-108 and pre-pro-BNP, and at least one BNP polypeptide selected from a second group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106; and specifically measuring a captured BNP polypeptide from the first group. Optionally, the specifically measuring step specifically measures an amount of at least one captured BNP polypeptide from the first group and an amount of at least one captured BNP polypeptide selected from the second group and the method further comprises determining relative ratio of the amounts of each specifically measured BNP polypeptide.

The invention further provides a method for discovering polypeptides that interact with a BNP fragment. The method entails capturing a BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106 with a biospecific capture reagent. Molecules that are not bound to the biospecific capture reagent or BNP fragment are removed. Molecules bound to the captured BNP fragment are measured. Optionally, the molecules are measured by affinity mass spectrometry.

The invention provides methods of determining a correlation between at least one specific measurement and a clinical parameter. The methods entails providing a learning set comprising a plurality of data objects representing subjects, wherein each data object comprises data representing a specific measurement of a BNP polypeptide selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-10; and (b) determining a correlation between at least one specific measurement and a clinical parameter. Optionally, providing the learning set comprises: capturing BNP polypeptides from a sample with an antibody, and specifically measuring one or more of the BNP polypeptides including the BNP fragment selected from the group.

The invention provides methods of classifying a data object according to clinical parameter. The methods entail providing a learning set comprising a plurality of data objects representing subjects, wherein each subject is classified into at least one of a plurality of different clinical parameters and wherein each data object comprises data representing specific measurement of a plurality of BNP polypeptides from a subject sample, and at least one BNP polypeptide is a BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106; and training a learning algorithm with the learning set, thereby generating a classification model, wherein the classification model classifies a data object according to clinical parameter.

Optionally, the clinical parameters are selected from presence or absence of disease; risk of disease, stage of disease; response to treatment of disease; and class of disease. Optionally, the learning set further comprises data representing specific measurement of a polypeptide interactor of a BNP polypeptide. Optionally, the learning algorithm is unsupervised. Optionally, the learning algorithm is supervised and each data object further comprises data representing the clinical parameter of the subject. Optionally, the classification model on subject data from a subject of unknown clinical parameter to classify the subject according to a clinical parameter. Optionally, the clinical parameter is presence or absence of acute coronary syndrome. Optionally, the supervised learning algorithm is selected from linear regression processes, binary decision trees, artificial neural networks, discriminant analyses, logistic classifiers, recursive partitioning processes, and support vector classifiers. Optionally, the supervised learning algorithm is a recursive partitioning process.

The invention further provides a method for qualifying an immunoassay calibrator for a BNP immunoassay. The method entails providing an immunoassay calibrator for a BNP immunoassay, wherein the calibrator comprises a designated concentration of one or more BNP polypeptides. Polypeptides from the calibrator are captured with an antibody to a BNP polypeptide. An amount of at least one polypeptide selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106 is specifically measured, whereby the measured amount provides an indication of the quality of the immunoassay calibrator. Optionally, the method further comprises specifically measuring at least one BNP polypeptide selected from the group consisting of BNP1-76, BNP77-108, BNP1-108, and pre-proBNP. Optionally, the method further comprises determining the amount of the at least one BNP polypeptide selected from the group consisting of BNP1-76, BNP77-108, BNP1-108, and pre-proBNP as a function of total polypeptide captured by the antibody. Optionally, the amount is measured by affinity mass spectrometry.

The invention further provides a method for qualifying an immunoglobulin reagent that specifically binds to a BNP polypeptide. The method entails analyzing the immunoglobulin reagent by mass spectrometry; and determining the relative amounts of intact immunoglobulin and immunoglobulin fragments in the reagent.

The invention further provides a method of measuring modified forms of an antibody to a BNP polypeptide in an antibody reagent for a BNP immunoassay. Optionally, the method further comprises measuring un-modified forms of the antibody in the reagent and comparing the measurement of un-modified antibody to the measurement of modified forms of the antibody. Optionally, the method further comprises specifically measuring the amount of at least one BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106 in the immunoassay calibration sample.

The invention further provides an antibody that specifically binds to at least one but not all of the BNP fragments selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. Optionally, the antibody specifically binds to one and only one of the BNP fragments selected from the group. Some antibodies distinguish at least one of the above fragments from at least another of the above fragments.

In one embodiment, an assay may be conducted using an antibody or antibody cocktail formulated to detect a plurality of natriuretic peptide (e.g., BNP) fragments as defined herein. The presence or amount of this plurality of fragments may provide a more accurate prognostic or diagnostic result than simply measuring the mature natriuretic peptide (or natriuretic peptide precursor) itself. For example, antibodies that detect only the mature natriuretic peptide, but that are not able to detect degradation fragments, may provide an aberrantly low assay result (e.g., indicating that no BNP or low BNP concentrations are present in the sample, when the BNP was present, but has been degraded).

In an alternative embodiment, individual antibodies that distinguish amongst a plurality of natriuretic peptide (e.g., BNP) fragments may be individually employed to separately detect the presence or amount of different fragments. The results of this individual detection may provide a more accurate prognostic or diagnostic result than detecting the plurality of fragments in a single assay. For example, different weighting factors may be applied to the various fragment measurements to provide a more accurate estimate of the amount of natriuretic peptide originally present in the sample. Additionally, the relative amounts of the various fragments may be used to estimate the length of time since the onset of an event since, as discussed above, production of such fragments may be a function of, inter alia, the elapsed time between onset of an event triggering natriuretic peptide release into the tissues and the time the sample is obtained or analyzed.

In related aspects, the purified natriuretic peptide fragments of the present invention may be employed in methods to generate antibodies that recognize one or a group of fragments. In various embodiments, a polypeptide may be selected that comprises a sequence that is common to a number of natriuretic peptide fragments, and used to generate antibodies that recognize this common sequence; such antibodies would recognize each of the fragments in which the sequence is in common and expressed such that binding is sterically possible. In alternative embodiments, a fragment may be selected that comprises a sequence that is distinctive to a specific fragment or set of fragments, and used to generate antibodies that recognize only that particular fragment or set of fragments. Such an antibody is said to "distinguish" the selected fragments from those fragments that are unrecognized by the antibody. Thus, the present invention also relates to antibodies selected to bind one or more preselected natriuretic peptide fragments, and methods for their generation and selection.

In various embodiments, the present invention relates to antibodies selected to bind to a plurality of BNP polypeptides selected from the group consisting of BNP77-108, BNP1-76, BNP1-108, pre-proBNP and/or the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. The present invention also relates to methods for the selection of such antibodies. Preferably, such antibodies are selected to bind to a plurality of BNP peptides generated from BNP77-108, more preferably to bind a plurality of BNP77-108, BNP77-106, BNP79-106, BNP76-107, BNP79-108, BNP80-108, BNP81-108, BNP83-108, and most preferably to each of BNP77-108, BNP77-106, BNP79-106, BNP76-107, BNP79-108, BNP80-108, BNP81-108, BNP83-108. In other preferred embodiments, antibodies are also selected to bind to BNP polypeptides regardless of methionine oxidation state.

In various embodiments, the present invention relates to antibodies selected to specifically bind to a plurality of BNP polypeptides selected from the group consisting of BNP77-108, BNP1-76, BNP1-108, pre-proBNP and/or the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. The present invention also relates to methods for the selection of such antibodies. Preferably, such antibodies are selected to bind specifically to a plurality of BNP peptides generated from BNP77-108, more preferably to bind a plurality of BNP77-108, BNP77-106, BNP79-106, BNP76-107, BNP79-108, BNP80-108, BNP81-108, BNP83-108, and most preferably to each of BNP77-108, BNP77-106, BNP79-106, BNP76-107, BNP79-108, BNP80-108, BNP81-108, BNP83-108. In other preferred embodiments, antibodies are also selected to bind specifically to BNP polypeptides regardless of methionine oxidation state.

In various alternative embodiments, the present invention relates to antibodies selected to distinguish between a first group comprising one or more BNP polypeptides selected from the group BNP77-108, BNP1-76, BNP1-108, pre-proBNP, BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106 and a second group comprising one or more different BNP polypeptides selected from the group consisting of BNP77-108, BNP1-76, BNP1-108, pre-proBNP, BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. The present invention also relates to methods for the selection of such antibodies. Preferably, members of the first and/or second groups comprise BNP peptides generated from BNP77-108, and most preferably members of the first and/or second groups comprise BNP77-108, BNP77-106, BNP79-106, BNP76-107, BNP79-108, BNP80-108, BNP81-108, BNP83-108. In other preferred embodiments, antibodies are also selected to distinguish BNP polypeptides on the basis of a methionine oxidation state.

In various embodiments, antibodies are selected, based not upon a particular affinity for one or more natriuretic peptide fragments, but instead based upon a signal that is obtainable in a binding assay such as an immunoassay. Various binding assay formats are known in the art, and it is often the use of antibodies to formulate an appropriate assay that is more important than a particular affinity of an antibody for one or more target molecules. For example, competitive binding assays may comprise a receptor (e.g., an antibody) bound to a solid surface. An analyte of interest in a test sample competes for binding with a labeled molecule that also binds to the receptor. The amount of labeled molecule bound to the receptor (and hence assay signal) is inversely proportional to the amount of analyte of interest in the test sample. In this case, a single antibody attached to the solid phase is used. Alternatively, in a sandwich immunoassay, a first antibody, typically bound to a solid surface, and a second antibody, typically conjugated to a detectable label, each bind to an analyte of interest in a test sample. The amount of labeled molecule bound to the receptor (and hence assay signal) is directly proportional to the amount of analyte of interest in the test sample.

In yet another alternative, a sample may be mixed with one or more compounds that inhibit the production of natriuretic peptide (e.g., BNP) fragments. In such embodiments, one or more proteolytic inhibitors and/or chelators may be added to a biological sample to prevent degradation of the natriuretic peptide(s) fragments that may not be accurately detected by an assay.

The invention further provides a method of assaying BNP polypeptides. The method entails capturing one or more BNP polypeptides from a subject sample; and specifically measuring a presence or an amount of at least one captured BNP polypeptide from among those captured. Optionally, at least 3, 4, 5 or 10 BNP polypeptides are captured and specifically measured.

The invention further provides a method of classifying test samples. The method entails specifically measuring the presence or amount of one or more BNP polypeptides from each of a plurality of samples of a first class characterized by a BNP-related pathology. A presence or amount of said one or more BNP polypeptides is specifically measured from a plurality of samples of a second class, wherein the second class is characterized by absence of a BNP-related pathology. A classification model is developed based on the measurements that classify a test sample into the first class or the second class. At least one of the BNP polypeptides is other than BNP1-76, BNP77-108, BNP1-108, pre-pro-BNP.

The invention further provides a method for discovering polypeptides that interact with a BNP polypeptide. The method entails capturing a BNP polypeptide from a sample with a biospecific capture reagent; removing molecules that are not bound to the biospecific capture reagent or BNP polypeptide; and measuring molecules bound to the captured BNP polypeptide.

The invention further provides a method of correlating specific measurement of BNP polypeptides and the clinical parameters. The method entails providing a learning set comprising a plurality of data objects representing subjects, in which each data object comprises data representing a specific measurement of a BNP polypeptide from a subject sample and a clinical parameter of the subject. A correlation is determined between specific measurement of the BNP polypeptide and the clinical parameter(s). At least one of the BNP polypeptides is other than BNP1-76, BNP77-108, BNP1-108, pre-pro-BNP.

The invention further provides a method of specifically measuring a BNP polypeptide selected from the group consisting of BNP1-76, BNP77-108, BNP1-108 and pre-pro-BNP in a subject sample; and correlating the measurement with a clinical parameter of the subject. Optionally, the method further comprises specifically measuring at least one BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106 and correlating the measurements with the clinical parameter. Optionally, the method further comprises specifically measuring at least one biomolecular interactor of a BNP polypeptide or antibody to a BNP polypeptide, or a BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106; and correlating the measurement with the clinical parameter.

The invention further provides a method for qualifying an immunoassay calibrator for a BNP immunoassay. The method comprises providing an immunoassay calibrator for a BNP immunoassay, wherein the calibrator comprises a designated concentration of one or more BNP polypeptides; capturing polypeptides from the calibrator with an antibody to a BNP polypeptide; and (c) specifically measuring an amount of at least one BNP polypeptides whereby the measured amount provides an indication of the quality of the immunoassay calibrator.

The invention further provides biomolecular interactors with BNP or isolated biomolecular interactors of anti-BNP antibodies that can be found in biological samples. These biomolecular interactors were discovered through affinity mass spectrometry in which analytes from a biological sample were captured on a mass spectrometry probe with an anti-BNP antibody, and specifically detected and distinguished by laser desorption/ionization mass spectrometry from the capture surface. The interactors can be characterized by molecular weight.

In various embodiments, the present invention relates to immunoassays configured to provide a single signal that relates to the presence or amount of a plurality of BNP polypeptides selected from the group consisting of the group consisting of BNP77-108, BNP1-76, BNP1-108, pre-proBNP, BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. Preferably, such immunoassays configured to provide a single signal that is related to the presence or amount of a plurality of BNP peptides generated from BNP77-108, more preferably to a plurality of BNP77-108, BNP77-106, BNP79-106, BNP76-107, BNP79-108, BNP80-108, BNP81-108, BNP83-108, and most preferably to each of BNP77-108, BNP77-106, BNP79-106, BNP76-107, BNP79-108, BNP80-108, BNP81-108, BNP83-108. In other preferred embodiments, immunoassays are also configured to provide a single signal that relates to the presence or amount of BNP polypeptides regardless of methionine oxidation state.

In preferred embodiments, an immunoassay provides a signal that is within a factor of 5, and most preferably within a factor of two, from an equal number of molecules of a plurality of natriuretic peptide fragments, and most preferably a plurality of the foregoing BNP polypeptides.

In various alternative embodiments, the present invention relates to immunoassays configured to provide a signal that distinguishes between a first group comprising one or more BNP polypeptides selected from the group consisting of BNP77-108, BNP1-76, BNP1-108, pre-proBNP, BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106, and a second group comprising one or more different BNP polypeptides selected from the group consisting of BNP77-108, BNP1-76, BNP1-108, pre-proBNP, BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. Preferably, members of the first and/or second groups comprise BNP peptides generated from BNP77-108, and most preferably members of the first and/or second groups comprise BNP77-108, BNP77-106, BNP79-106, BNP76-107, BNP79-108, BNP80-108, BNP81-108, BNP83-108. In other preferred embodiments, immunoassays are also configured to distinguish BNP polypeptides depending upon methionine oxidation state.

In yet another aspect, the present invention relates to standard solutions comprising a known amount of one or more purified, and preferably substantially purified, natriuretic peptide fragments other than mature ANP, BNP, and CNP, their precursor molecules, and the fragments generated by cleavage of the precursor molecules into the mature ANP, BNP, and CNP peptides. Such standard solutions may find use as positive and/or negative control samples in the various assays described herein. In various embodiments, the present invention relates to any purified, and preferably substantially purified, BNP polypeptide(s) other than pre-proBNP, BNP1-108, BNP1-76, and BNP77-108. In preferred embodiments, the present invention relates to one or more standard solutions comprising a known amount of one or more purified, and preferably substantially purified-related polypeptides selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106.

In certain aspects, it may be advantageous to formulate such standard solutions or calibrants using a composition that is substantially equivalent to the test sample; for example, the solution may comprise blood, serum, plasma, etc., as a solvent for the natriuretic peptide fragment(s) of interest. In such a case, it may also be advantageous to include one or more protease inhibitors or chelators in order to prevent degradation of the added natriuretic peptide fragment(s).

In another aspect, one or more antibodies, antibody conjugates, and/or standard solutions of the present invention may be provided as kits for determining the presence or amount of natriuretic peptide fragments. These kits preferably comprise devices and reagents for performing at least one assay as described herein on a test sample. Such kits preferably contain sufficient reagents to perform one or more such determinations, and/or Food and Drug Administration (FDA)-approved labeling.

In still another aspect, the invention relates to methods for determining a treatment regimen for use in a patient. The methods preferably comprise determining the presence or amount of one or more natriuretic peptide fragments other than mature ANP, BNP, and CNP, their precursor molecules, and the fragments generated by cleavage of the precursor molecules into the mature ANP, BNP, and CNP peptides, and relating this presence or amount to a disease or prognostic state. As discussed herein, diagnosis and differentiation of various cardiovascular and cerebrovascular diseases, including stroke, congestive heart failure (CHF), cardiac ischemia, systemic hypertension, and/or acute myocardial infarction may be related to ANP, BNP, and/or CNP levels. Once a diagnosis is obtained, a treatment regimen is selected to be consistent with that diagnosis.

In yet another aspect, the present invention relates to methods of identifying novel polypeptides present in biological samples, preferably blood, serum, or plasma samples, that are related to known polypeptides. In these methods, an antibody having an affinity for one or more known polypeptides (e.g., BNP) is used as an affinity probe for binding additional polypeptides that are sufficiently related in structure so as to share binding affinity to the antibody, but that are previously unpredicted as being present in the sample. The sequence of the polypeptide(s) is(are) then obtained by the methods described herein. Once obtained, the sequence may be used in the other aspects described herein; e.g., to select antibodies that can differentiate the known polypeptide(s) and the previously unknown polypeptides, again according to the methods described herein; to determine if the previously unknown polypeptides are useful as diagnostic or prognostic markers; and/or to provide standard solutions or isolated peptides.

In one aspect, a method is described which qualifies an antibody in an antibody reagent for tagged immunoassay by mass spectroscopy methods such as SELDI. In a further aspect, the method is used to qualify the antibody by determining the amount of antibody as a function of total protein of a sample. In a detailed aspect, the method further includes preparing an antibody reagent in which the amount of antibody in the reagent comprises the same amount reflected in the amount of antibody from the sample as determined by SELDI.

In another aspect, a method is described which qualifies peptides in a calibrator for tagged immunoassay by SELDI. In a further aspect, the method is used to qualify peptides by determining the amount of one or more particular peptides as a function of total protein in a sample. In a detailed aspect, the method further includes preparing a peptide reagent in which the amount of peptide in the reagent comprises an amount reflected in the amount of peptide from the sample as determined by SELDI.

In a further aspect, the method includes qualifying an antibody in an antibody reagent for a tagged immunoassay using a SELDI immunoassay. In a detailed aspect, the tagged immunoassay is a BNP immunoassay. In a further detailed aspect, SELDI is SEAC. In a further detailed aspect, SELDI is SEND.

In another aspect, a method is described which includes the steps of qualifying the polypeptides captured by an antibody reagent in a tagged immunoassay by providing a SELDI probe comprising the antibody reagent attached to a surface of the probe, contacting the antibody reagent with a sample, whereby the antibody reagent captures polypeptides from the sample, and detecting the captured polypeptides by SELDI. In a detailed aspect, the tagged immunoassay is a BNP immunoassay. In a further detailed aspect, SELDI is SEAC. In a further detailed aspect, SELDI is SEND.

BRIEF DESCRIPTION OF THE DRAWINGS

FIG. 1. Predicted amino acid sequence (SEQ ID NO:1) of B-type Natriuretic Peptide (BNP) Precursor and fragments thereof is shown. Fragment Arg77-His108 (indicated on the figure as "77-108") is one isoform sought to be detected by immunoassay.

FIGS. 7A and B. Mass spectra of subject samples. Peaks corresponding to BNP77-109 are difficult to detect. However, degraded forms of BNP appear to be present—about 3152 (BNP77-106) and about 3282 (BNP79-108).

DEFINITIONS

Figure 2A:
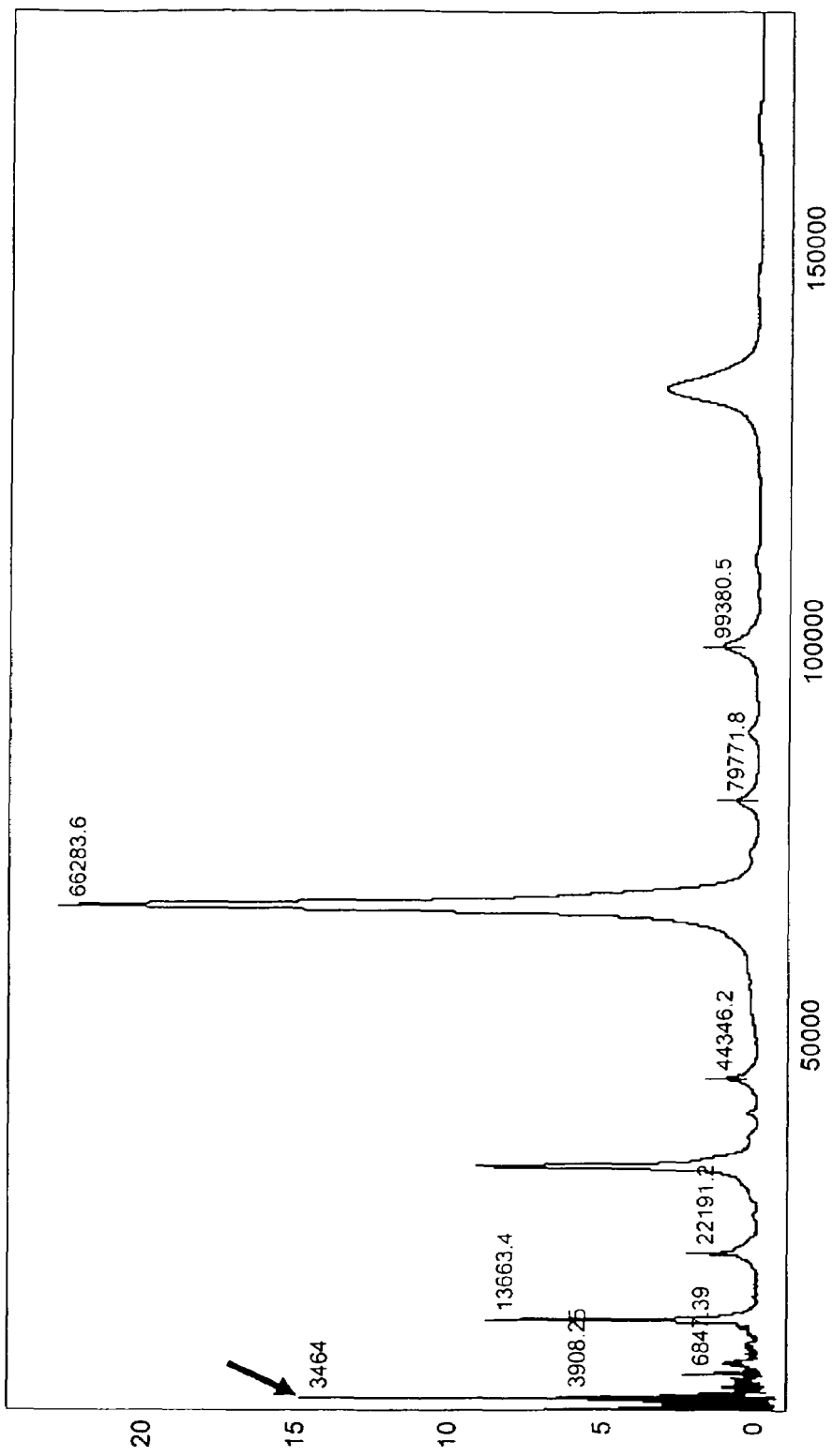
FIGS. 2A and B. Mass spectra of proteins in a BNP immunoassay calibrator solution. SELDI analysis of a calibrator used for BNP immunoassays demonstrates that the calibrator contains many polypeptides besides full length BNP (BNP77-108). The peak at 3464 corresponds to BNP77-108. The peak at 66283.6 presumably corresponds to bovine serum albumin.

Human BNP is derived by proteolysis of a 108 amino acid precursor molecule, referred to hereinafter as BNP1-108. Mature BNP, or "the BNP natriuretic peptide," is a 32 amino acid molecule representing amino acids 77-108 of this precursor, and is referred to hereinafter as BNP77-108. The remaining residues 1-76 are referred to hereinafter as BNP1-76.

The sequence of the 108 amino acid BNP precursor pro-BNP (BNP1-108) is as follows, with mature BNP (BNP77-108) underlined:

```
HPLGSPGSAS DLETSGLQEQ RNHLQGKLSE LQVEQTSLEP LQESPRPTGV   50 (SEQ ID NO: 1)

WKSREVATEG IRGHRKMVLY TLRAPRSPKM VQGSGCFGRK MDRISSSSGL  100

GCKVLRRH.                                              108
```

BNP1-108 is synthesized as a larger precursor pre-pro-BNP having the following sequence (with the "pre" sequence shown in bold):

MDPQTAPSRA LLLLLFLHLA FLGGRSHPLG SPGSASDLET SGLQEQRNHL   50 (SEQ ID NO: 2)

QGKLSELQVE QTSLEPLQES PRPTGVWKSR EVATEGIRGH RKMVLYTLRA   100

PR<u>SPKMVQGS GCFGRKMDRI SSSSGLGCKV LRRH</u>.   134

The sequence of the 126 amino acid ANP precursor pro-ANP (ANP1-126) is as follows, with mature ANP (ANP99-126) underlined:

NPMYNAVSNA DLMDFKNLLD HLEEKMPLED EVVPPQVLSD PNEEAGAALS   50 (SEQ ID NO: 3)

PLPEVPPWTG EVSPAQRDGG ALGRGPWDSS DRSALLKSKL RALLTAPR<u>SL</u>   100

<u>RRSSCFGGRM DRIGAQSGLG CNSFRY</u>.   126

ANP1-126 is synthesized as a larger precursor pre-pro-ANP having the following sequence (with the "pre" sequence shown in bold):

MSSFSTTTVS FLLLLAFQLL GQTRANPMYN AVSNADLMDF KNLLDHLEEK   50 (SEQ ID NO: 4)

MPLEDEVVPP QVLSDPNEEA GAALSPLPEV PPWTGEVSPA QRDGGALGRG   100

PWDSSDRSAL LKSKLRALLT APR<u>SLRRSSC FGGRMDRIGA QSGLGCNSFR</u>   150

<u>Y</u>.   151

The sequence of the 126 amino acid CNP precursor pro-CNP (CNP1-126) is as follows, with the mature CNP forms CNP-53 (CNP74-126) in italics, and CNP-22 (CNP105-126) underlined:

MHLSQLLACA LLLTLLSLRP SEAKPGAPPK VPRTPPAEEL AEPQAAGGGQ   50 (SEQ ID NO: 5)

KKGDKAPGGG GANLKGDRSR LL*RDLRVDTK SRAAWARLLQ EHPNARKYKG*   100

*ANKK*<u>*GLSKGC FGLKLDRIGS MSGLGC*</u>.   126

The term "BNP polypeptide" refers to any of BNP1-76, BNP77-108, BNP1-108, pre-proBNP, and fragments thereof, including BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106.

The term "fragment" as used herein refers to a polypeptide that comprises at least six contiguous amino acids of a polypeptide from which the fragment is derived. Thus, a fragment of BNP1-108 (pro-BNP) refers to a polypeptide that comprises at least six contiguous amino acids of BNP1-108; a fragment of mature BNP refers to a polypeptide that comprises at least six contiguous amino acids of BNP77-108; a fragment of the polypeptide generated by cleavage of pro-BNP into mature BNP refers to a polypeptide that comprises at least six contiguous amino acids of BNP1-76. A "BNP" fragment means a fragment of any of BNP77-108, BNP1-76, BNP1-108 and pre-pro-BNP. Similarly, a fragment of ANP1-126 (pro-ANP) refers to a polypeptide that comprises at least six contiguous amino acids of ANP1-126; a fragment of mature ANP refers to a polypeptide that comprises at least six contiguous amino acids of ANP99-126; a fragment of the polypeptide generated by cleavage of pro-ANP into mature ANP refers to a polypeptide that comprises at least six contiguous amino acids of BNP1-98; and a fragment of CNP1-126 (pro-CNP) refers to a polypeptide that comprises at least six contiguous amino acids of CNP1-126; a fragment of mature CNP refers to a polypeptide that comprises at least six contiguous amino acids of CNP74-126 or CNP105-126; a fragment of the polypeptide generated by cleavage of pro-CNP into mature CNP refers to a polypeptide that comprises at least six contiguous amino acids of CNP1-73 or CNP1-104. In preferred embodiments, a fragment refers to a polypeptide that comprises at least 10 contiguous amino acids of a polypeptide from which the fragment is derived; at least 15 contiguous amino acids of a polypeptide from which the fragment is derived; or at least 20 contiguous amino acids of a polypeptide from which the fragment is derived.

The term "natriuretic peptide fragment" as used herein refers to a fragment, as described above, of any natriuretic peptide selected from the group consisting of mature ANP, BNP, or CNP, the biosynthetic precursors pre-pro-ANP, pre-pro-BNP, pre-pro-CNP, pro-ANP, pro-BNP, or pro-CNP, or the polypeptide remaining after removal of mature ANP, BNP, or CNP from the pro-form of the peptide.

Unless otherwise apparent from the context, reference to natriuretic polypeptides includes modified forms of polypeptides bearing post-translational modification including, for example, phosphorylation (adds 80 D per phosphate group), glycosylation, lipidation, methylation (adds 14 D per methyl group), cysteinylation (adds 199 D per cysteinyl group), sulphonation, glutathionylation (adds 305 D per glutathione group), and acetylation (adds 42 D per acetyl group). Natriuretic peptide fragments, including BNP polypeptide can comprise one or more oxidizable methionines, the oxidation of which to methionine sulfoxide or methionine sulfone. Changes in the oxidation state of one or more methionines may alter the ability of assays to detect such fragments. Thus, in addition to the reduced forms of the substantially purified natriuretic peptide fragments discussed above, the present invention also relates to one or more purified, and preferably substantially purified, natriuretic peptide fragments other than mature ANP, BNP, and CNP, their precursor molecules, and the fragments generated by cleavage of the precursor molecules into the mature ANP, BNP, and CNP peptides, in which one or more methionines are oxidized. Preferred are one or more substantially purified BNP polypeptides selected from the group consisting of BNP77-108, BNP1-76, BNP1-108, pre-proBNP and the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106 in which one or more methionines are oxidized. The presence or absence of natriuretic peptide fragments in which one or more of these peptides may be measured by immunoassay, mass spectrometry, high pressure liquid chromatography and gas chromatography, as described hereinafter.

Most preferably, a fragment is "naturally present" in a biological sample (e.g., a blood, serum or plasma sample, and most preferably human blood, serum, or plasma). This means that the fragment may be obtained from an unsupplemented biological sample obtained from a human or animal. "Unsupplemented" refers to a sample in which the fragment or its precursor has not been exogenously added once the sample is obtained. Examples of fragments naturally present in blood, serum or plasma are described hereinafter. Other preferred fragments are said to be "generated from" blood, serum or plasma if the fragment is present as a result of supplementing such a sample with pro-ANP, pro-BNP, pro-CNP, and/or a fragment thereof, and allowing endogenous factors (e.g., proteases) in the sample to generate additional fragments. Examples of fragments generated from human blood, serum or plasma are also described hereinafter. A fragment is "present" in blood, serum or plasma if the fragment is either naturally present or generated from such a sample.

As used herein, the term "purified" in reference to polypeptides does not require absolute purity. Instead, it represents an indication that the polypeptide(s) of interest is(are) in a discrete environment in which abundance (on a mass basis) relative to other proteins is greater than in a biological sample. By "discrete environment" is meant a single medium, such as a single solution, a single gel, a single precipitate, etc. Purified polypeptides may be obtained by a number of methods including, for example, laboratory synthesis, chromatography, preparative electrophoresis, centrifugation, precipitation, affinity purification, etc. One or more "purified" polypeptides of interest are preferably at least 10% of the protein content of the discrete environment. One or more "substantially purified" polypeptides are at least 50% of the protein content of the discrete environment, more preferably at least 75% of the protein content of the discrete environment, and most preferably at least 95% of the protein content of the discrete environment. Protein content is determined using a modification of the method of Lowry et al., *J. Biol. Chem.* 193: 265, 1951, described by Hartree, *Anal Biochem* 48: 422-427 (1972), using bovine serum albumin as a protein standard.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. Natural immunoglobulins are encoded by immunoglobulin genes. These include the kappa and lambda light chain constant region genes, the alpha, gamma, delta, epsilon and mu heavy chain constant region genes, and the myriad immunoglobulin variable region genes. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; an scFv protein, which is a fusion protein in which a light chain variable region and a heavy chain variable region bound by a linker; and (vii) an isolated complementarity determining region (CDR). The "Fc" portion of an antibody refers to that portion of an immunoglobulin heavy chain that comprises one or more heavy chain constant region domains, CH1, CH2 and CH3, but does not include the heavy chain variable region. Single chain antibodies, monoclonal antibodies, polyclonal antibodies, chimeric antibodies, humanized antibodies, and antibodies produced by immunization, from hybridomas, or recombinantly using molecular biological techniques (e.g., by phage display methods) are also included by reference in the term "antibody."

Individual antibodies (e.g., obtained by phage display or monoclonal antibody technology) may be obtained that bind to a plurality of fragments having a common epitope to which the antibody may bind. In the alternative, individual antibodies may be pooled to provide the desired spectrum of binding affinities. The term "antibody" may refer to both a composition in which each antibody molecule present is identical (referred to specifically as an "individual antibody"), or a composition in which antibody molecules present may differ (e.g., in a pooled or polyclonal composition). Preferred antibodies are "Omniclonal" antibodies. Omniclonal antibodies are a mixture of different antibody molecules selected from a phage display library, where each antibody specifically binds to a target antigen with a minimum affinity of $10^9$ M$^{-1}$ to $10^{10}$ M$^{-1}$.

"Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in METHODS IN MOLECULAR BIOLOGY, Vol. 66, Glenn E. Morris, ed (1996).

The term "specifically binds" does not necessarily require that an antibody binds exclusively to its intended target. Rather, an antibody specifically binds if its affinity for its intended target is about 2-fold greater when compared to its affinity for a non-target molecule. Preferably the affinity of the antibody will be at least about five fold, preferably 10 fold, more preferably 25-fold, even more preferably 50-fold, and most preferably 100-fold or more, greater for a target molecule than its affinity for a non-target molecule. In preferred embodiments, specific binding between an antibody or other binding agent and an antigen means a binding affinity of at least $10^6$ $M^{-1}$. Preferred antibodies bind with affinities of at least about $10^7$ $M^{-1}$, and preferably $10^8$ $M^{-1}$ to $10^9$ $M^{-1}$ or $10^{10}$ $M^{-1}$. A ligand or a receptor that "specifically binds" to a compound analyte can be used to determine the presence or amount of the analyte in a sample of unrelated heterogeneous compounds. Thus, the ligand or receptor binds preferentially to a particular analyte and does not bind in a significant amount to the other compounds present in the sample. For example, an antibody specifically binds under immunoassay conditions to an antigen analyte bearing an epitope against which the antibody was raised.

An immunoassay is said to "distinguish" between a first group of polypeptides and a second group of polypeptides if the immunoassay provides a signal related to binding of the first group of polypeptides that is at least a factor of 10 greater than a signal obtained from an equal number of molecules of the second group of polypeptides under the same assay conditions. More preferably, the signal is at least a factor of 20 greater, even more preferably at least a factor of 50 greater, and most preferably at least a factor of 100 greater or more.

An antibody is said to "distinguish" between a first group of polypeptides and a second group of polypeptides if its affinity for the members of the first group of polypeptides is about 2-fold greater when compared to its affinity for members of the second group. Preferably the affinity of the antibody will be at least about five fold, preferably 10 fold, more preferably 25-fold, even more preferably 50-fold, and most preferably 100-fold or more, greater for members of the first group of polypeptides than its affinity for members of the second group.

A molecule is "specifically measured" when its presence and/or amount is detected in a sample to the exclusion of other molecules that are structurally related. One BNP polypeptide selected from the group consisting of BNP79-108, BNP77-106, BNP39-86, BNP53-85, BNP66-98, BNP30-106, BNP11-107, BNP9-106, BNP69-100, BNP76-107 BNP69-108, BNP80-108, BNP81-108, BNP83-108, BNP30-103, BNP3-108 and BNP79-106 is specifically measured, when the measurement detects that polypeptide in a manner distinguishable from measurement of any other BNP polypeptide in the group, and distinguishable from any measurement of BNP polypeptides BNP1-76, BNP77-108, BNP1-108, and pre-proBNP. BNP77-106 fragment is specifically measured when its presence and/or amount are detected or quantified, wherein the presence and/or amount of other BNP fragments such as BNP77-108 do not contribute to a signal that constitutes a specific measurement of BNP77-106.

A signal from an immunoassay is said to "depend upon binding to an antibody" if the antibody participates in formation of a complex necessary to generate the signal. For example, in a sandwich immunoassay formulated using a solid phase antibody and a second antibody conjugate, each of which must bind to an analyte to form the sandwich, each of the solid phase antibody and second antibody participate in formation of the complex necessary to generate the signal. In a competitive immunoassay where a single antibody is used, and an analyte competes with an analyte conjugate for binding, the single antibody participates in formation of the complex necessary to generate the signal. Numerous additional immunoassay formulations may be provided.

The term "plurality" as used herein in reference to natriuretic peptide fragments and BNP polypeptides refers to 2 or more molecular species that differ in amino acid sequence.

An "interactor" is a molecule that specifically binds to another molecule.

"Immunoassay" refers to a method of detecting an analyte in a sample in which specificity for the analyte is conferred by the specific binding between an antibody and a ligand such as a natriuretic peptide fragment. This includes detecting an antibody analyte through specific binding between the antibody and a ligand. See Harlow and Lane (1988) ANTIBODIES, A LABORATORY MANUAL, Cold Spring Harbor Publications, New York, for a description of immunoassay formats and conditions that can be used to determine specific immunoreactivity. A "tagged immunoassay" is an immunoassay in which the analyte is not detected directly, but rather through detection of a tag or label. Generally, the analyte is itself tagged, or the immunoassay involves binding of the analyte with a tagged antibody which is, itself, tagged. The techniques of immunoassay using labeled reagents for detecting antigens and antibodies are sensitive. Solid-phase assays for antibodies employing ligands labeled with radioisotopes or enzymes (radioimmunoassay; RIA and enzyme-linked immunosorbent assay; ELISA) are widely used because large numbers can be performed in a relatively short time. RIA and ELISA are direct binding assays for antibody (or antigen) and both work on the same principle, but the means of detecting specific binding is different. For both methods, a pure preparation of a known antigen or antibody, or both, is needed in order to standardize the assay. In RIA for an antigen, pure antibody against that antigen is radioactively labeled, usually with $^{125}$I; for the ELISA, an enzyme is linked chemically to the antibody. The unlabeled component, which in this case is the antigen, is attached to a solid support, such as the wells of a plastic multiwell plate, which will adsorb a certain amount of any protein. The labeled antibody is allowed to bind to the unlabeled antigen, under conditions where nonspecific adsorption is blocked, and any unbound antibody and other proteins are washed way. Antibody binding in RIA is measured directly in terms of the amount of radioactivity retained by the coated wells, whereas in ELISA, binding is detected by a reaction that converts a colorless substrate into a colored reaction product. Labeled anti-immunoglobulin antibodies can also be used with RIA or ELISA to detect binding of unlabeled antibody to unlabeled antigen-coated plates. Alternatively, the immunoassay may be a SELDI MS immunoassay. An immunoassay based on mass spectrometry automatically provides discrimination of the various captured polypeptides based on mass.

A modification of ELISA known as a "capture" or "sandwich ELISA" (or more generally referred to as an "antigen-capture assay") can be used to detect secreted products such as cytokines. Rather than the antigen being directly attached to a plastic plate, antigen-specific antibodies are bound to the plate. These are able to bind antigen with high affinity, and thus concentrate it on the surface of the plate, even with antigens that are present in very low concentrations in the initial mixture. A separate labeled antibody that recognizes a different epitope to the immobilized first antibody is then used to detect the bound antigen.

RIA and ELISA do not allow one to measure directly the amount of antigen or antibody in a sample of unknown composition, as both depend on the binding of a pure labeled antigen or antibody. In a "competitive inhibition assay," the presence and amount of a particular antigen in an unknown sample is determined by its ability to compete with a labeled reference antigen for binding to an antibody typically attached to a plastic well. A standard curve is first constructed by adding varying amounts of a known, unlabeled standard preparation; the assay can then measure the amount of antigen in unknown samples by comparison with the standard. The competitive binding assay can also be used for measuring antibody in a sample of unknown composition by attaching the appropriate antigen to the plate and measuring the ability of the test sample to inhibit the binding of a labeled specific antibody.

A molecule such as an antibody can be "qualified" in terms of the amount of the molecule, its binding specificity, and/or its quality, e.g., its state of degradation. For example, methods of qualifying the peptides in an immunoassay calibrator, e.g., a BNP immunoassay calibrator, can be performed by mass spectrometry, in particular by SELDI. SELDI allows more precise discrimination of those peptides, as they can be both discriminated according to mass and quantified based on the area under a mass spectrum peak. Because mass spectrometry qualifies molecules by mass, polypeptides comprising the same epitope, but differing in mass may be detected, differentiated and measured.

"Detectable moiety" or a "label" or a "tag" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, digoxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety can be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner can itself be directly detectable, for example, an antibody can be itself labeled with a fluorescent molecule. The binding partner also can be indirectly detectable, for example, a nucleic acid having a complementary nucleotide sequence can be a part of a branched DNA molecule that is in turn detectable through hybridization with other labeled nucleic acid molecules. (See, e.g., P. D. Fahrlander and A. Klausner, Bio/Technology 6:1165 (1988)). Quantitation of the signal is achieved by, e.g., scintillation counting, densitometry, or flow cytometry.

Devices for performing the assays described herein preferably contain a plurality of discrete, independently addressable locations, or "diagnostic zones," each of which is related to a particular peptide or set of peptides of interest. For example, each of a plurality of discrete zones may comprise a receptor (e.g., an antibody) for binding a different peptide. Alternatively, one or more zones may each comprise a receptor (e.g., an antibody) for binding a plurality of peptides. Following reaction of a sample with the devices, a signal is generated from the diagnostic zone(s), which may then be correlated to the presence or amount of the peptide of interest. In some instances "diagnostic zones" are also referred to as "addressable locations."

The term "discrete" as used herein refers to areas of a surface that are non-contiguous. That is, two areas are discrete from one another if a border that is not part of either area completely surrounds each of the two areas. The term "independently addressable" as used herein refers to discrete areas of a surface from which a specific signal may be obtained. Antibody zones can also be independent of each other, but can be in contact with each other on a surface. For example, antibodies that recognize different epitopes of a single antigen can each be attached to the surface of a biochip that comprises a plurality of addressable locations, each of which location has an antibody attached there The team "sample" refers to a quantity of biological molecules that are to be tested for the presence or absence of one or more molecules.

The term "test sample" as used herein refers to a sample in which the presence or amount of one or more analytes of interest are unknown and to be determined in an assay, preferably an immunoassay. Preferably, a test sample is a bodily fluid obtained for the purpose of diagnosis, prognosis, or evaluation of a subject, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. Some test samples are more readily analyzed following a fractionation or purification procedure, for example, separation of whole blood into serum or plasma components. Preferred samples may be obtained from bacteria, viruses and animals, such as dogs and cats. Particularly preferred samples are obtained from humans. By way of contrast, a "standard sample" refers to a sample in which the presence or amount of one or more analytes of interest are known prior to assay for the one or more analytes. Some test samples obtained from patients are referred to as "test samples."

The term "disease sample" as used herein refers to a tissue sample obtained from a subject that has been determined to suffer from a given disease. Methods for clinical diagnosis are well known to those of skill in the art. See, e.g., *Kelley's Textbook of Internal Medicine*, 4th Ed., Lippincott Williams & Wilkins, Philadelphia, Pa., 2000; *The Merck Manual of Diagnosis and Therapy*, 17th Ed., Merck Research Laboratories, Whitehouse Station, N.J., 1999. "Disease" includes events generally accepted in the medical field as adverse outcomes related to a disease, such as stroke, myocardial infarction, and other adverse health events.

A pathological level of BNP refers to a statistically significant variation ($p \leq 0.05$), usually an increase, of BNP polypeptide(s) in a patient relative to mean levels in a population of undiseased individuals. A BNP related-pathology means a disease due to or otherwise associated with a pathological level of at least one BNP polypeptide or a mixture thereof. Such diseases include cardiovascular diseases, for example, stroke, congestive heart failure (CHF), cardiac ischemia, systemic hypertension, acute myocardial infarction, and acute coronary syndrome.

The presence or amount of one or more natriuretic peptide fragments of interest may be related to the presence or absence of a disease, or the likelihood of a future adverse outcome related to a disease. However, the signal obtained from an assay need not be related to the presence or amount of one or more natriuretic peptide fragments; rather, the signal may be directly related to the presence or absence of a disease, or the likelihood of a future adverse outcome related to a disease. For example, a level of signal x may indicate that y pg/mL of a fragment is present in the sample. A table may then indicate that y pg/mL of that fragment indicates congestive heart failure. It may be equally valid to simply relate a level of signal x directly to congestive heart failure, without determining how much of the fragment is present. Such a signal is preferably obtained from an immunoassay using the antibodies of the present invention, although other methods are well known.

The term "unpredicted polypeptides" as used herein refers to a polypeptide that, in the particular type of biological sample being analyzed, has not previously been demonstrated to be naturally present. A polypeptide is preferably unpredicted in a blood, serum, or plasma sample, and most preferably a human blood, serum, or plasma sample.

The term "determining the amino acid sequence" as used herein refers to methods by which the amino acid sequence of a particular polypeptide is obtained. Such methods may include direct sequencing (e.g., by Edman degradation); identification by mass spectrometry, which may comprise comparison of observed m/z to a predicted or known polypeptide sequence (see, e.g., Cagney and Emili, *Nature Biotechnol.* 20: 163-170 (2002)); peptide mapping; etc.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," *Prostate Cancer and Prostatic Diseases* 2: 264-76 (1999); and Merchant and Weinberger, "Recent advancements in surface-enhanced laser desorption/ionization-time of flight-mass spectrometry," *Electrophoresis* 21: 1164-67 (2000), each of which is hereby incorporated by reference in its entirety, including all tables, figures, and claims.

For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

Moreover, one can often enhance the resolution of the MS technique by employing "tandem mass spectrometry," or "MS/MS." In this technique, a precursor ion or group of ions generated from a molecule (or molecules) of interest may be filtered in an MS instrument, and these precursor ions subsequently fragmented to yield one or more fragment ions that are then analyzed in a second MS procedure. By careful selection of precursor ions, only ions produced by certain analytes of interest are passed to the fragmentation chamber, where collision with atoms of an inert gas occurs to produce the fragment ions. Because both the precursor and fragment ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF"), or surface-enhanced laser desorption ionization coupled with time-of-flight analyzers ("SELDI-TOF"), permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS" and "MS/MS-TOF," including MS/MS-MALDI-TOF and MS/MS-SELDI-TOF. Preferred apparatuses and methods for characterization and identification of proteins are disclosed in U.S. patent application Publication No. US 2002/0182649; U.S. Pat. No. 6,225,047; Issaq et al., *Biochem. Biophys. Res. Commun.* 292: 587-92 (2002); and Issaq et al., *Anal. Chem.* 75: 149A-155A (2003), each of which is hereby incorporated by reference in its entirety.

Ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy. In general, a probe with an adsorbent surface is contacted with a sample for a period of time sufficient to allow biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

One version of SELDI is called "affinity mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent may be attached directly to the substrate of the selective surface, or the substrate may have a reactive surface that carries a reactive moiety that is capable of binding the capture reagent, e.g., through a reaction forming a covalent or coordinate covalent bond. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbents" include those adsorbent materials typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbents" include those molecules that specifically bind to a biomolecule. Typically they comprise a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

In some embodiments, a SEAC probe is provided as a pre-activated surface which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Adsorption" refers to detectable non-covalent binding of an analyte to an adsorbent or capture reagent.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecyl-methacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

In another mass spectrometry method, the biomarkers can be first captured on a chromatographic resin that binds the target molecules. For example, the resin can be derivatized with an anti-BNP antibody. Alternatively, this method could be preceded by fractionating the sample on an anion exchange resin before application to the cation exchange resin. After elution from the resin, the sample can be analyzed by MALDI, electrospray, or another ionization method for mass spectrometry. In another alternative, one could fractionate on an anion exchange resin and detect by MALDI or electrospray mass spectrometry directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI, SELDI, electrospray mass spectrometry or another ionization mass spectrometry method.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed.

"Molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Monitoring" refers to recording changes in a parameter at multiple time points. Optionally, the parameter is continuously varying.

"Solid support" refers to a solid material which can be derivatized with, or otherwise attached to, a chemical moiety, such as a capture reagent, a reactive moiety or an energy absorbing species. Exemplary solid supports include chips (e.g., probes), microtiter plates and chromatographic resins.

"Chip" refers to a solid support having a generally planar surface to which a chemical moiety can be attached. Chips that are adapted to engage a probe interface are also called "probes."

"Biochip" refers to a chip to which a chemical moiety is attached. Frequently, the surface of the biochip comprises a plurality of addressable locations, each of which location has the chemical moiety attached there.

"Protein biochip" refers to a biochip adapted for the capture of polypeptides. Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, IMAC-30 and IMAC 40 (metal chelate); and PS-10, PS-20 (reactive surface with carboimidizole, expoxide) and PG-20 (protein G coupled through carboimidizole). These protein biochips comprise an aluminum substrate in the form of a strip. The surface of the strip is coated with silicon dioxide. In the case of the NP-20 biochip, silicon oxide functions as a hydrophilic adsorbent to capture hydrophilic proteins. Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitriloacetic acid functionalities that adsorb transition metal ions, such as copper, nickel, zinc, and gallium, by chelation. Preactivated ProteinChip arrays have carboimidizole or epoxide functional groups that can react with groups on proteins for covalent binding.

H4, H50, SAX-2, Q-10, WCX-2, CM-10, IMAC-3, IMAC-30, PS-10 and PS-20 biochips further comprise a functionalized, cross-linked polymer in the form of a hydrogel physically attached to the surface of the biochip or covalently attached through a silane to the surface of the biochip. The H4 biochip has isopropyl functionalities for hydrophobic binding. The H50 biochip has nonylphenoxy-poly(ethylene glycol)methacrylate for hydrophobic binding. The SAX-2 and Q-10 biochips have quaternary ammonium functionalities for anion exchange. The WCX-2 and CM-10 biochips have carboxylate functionalities for cation exchange. The IMAC-3 and IMAC-30 biochips have nitriloacetic acid functionalities that adsorb transition metal ions, such as $Cu^{++}$ and $Ni^{++}$, by chelation. These immobilized metal ions allow adsorption of peptide and proteins by coordinate bonding. The PS-10 biochip has carboimidizole functional groups that can react with groups on proteins for covalent binding. The PS-20 biochip has epoxide functional groups for covalent binding with proteins. The PS-series biochips are useful for binding biospecific adsorbents, such as antibodies, receptors, lectins, heparin, Protein A, biotin/streptavidin and the like, to chip surfaces where they function to specifically capture analytes from a sample. The PG-20 biochip is a PS-20 chip to which Protein G is attached. The LSAX-30 (anion exchange), LWCX-30 (cation exchange) and IMAC-40 (metal chelate) biochips have functionalized latex beads on their surfaces. Such biochips are further described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application US 2003 0032043 A1 (Pohl and Papanu, "Latex Based Adsorbent Chip," Jul. 16, 2002) and U.S. patent application 60/350,110 (Um et al., "Hydrophobic Surface Chip," Nov. 8, 2001); U.S. patent application 60/367,837, (Boschetti et al., "Biochips With Surfaces Coated With Polysaccharide-Based Hydrogels," May 5, 2002) and U.S. patent application entitled "Photocrosslinked Hydrogel Surface Coatings" (Huang et al., filed Feb. 21, 2003).

Such biochips are further described in: U.S. Pat. No. 6,579,719 (Hutchens and Yip, "Retentate Chromatography," Jun. 17, 2003); PCT International Publication No. WO 00/66265 (Rich et al., "Probes for a Gas Phase Ion Spectrometer," Nov. 9, 2000); U.S. Pat. No. 6,555,813 (Beecher et al., "Sample Holder with Hydrophobic Coating for Gas Phase Mass Spectrometer," Apr. 29, 2003); U.S. patent application No. U.S. 2003 0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Provisional Patent Application No. 60/367,837 (Boschetti et al., "Biochips With Surfaces Coated With Polysaccharide-Based Hydrogels," May 5, 2002) and U.S. patent application No. 60/448,467, entitled "Photocrosslinked Hydrogel Surface Coatings" (Huang et al., filed Feb. 21, 2003).

Many protein biochips, adapted for the capture of polypeptides, are described in the art. These include, for example, protein biochips produced by Ciphergen Biosystems (Fremont, Calif.), Packard BioScience Company (Meriden Conn.), Zyomyx (Hayward, Calif.), Phylos (Lexington, Mass.) and Procognia (Sense Proteomic Limited) (Maidenhead, Berkshire, UK). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001), International publication WO 00/56934 (Englert et al., "Continuous porous matrix arrays," Sep. 28, 2000), U.S. patent publication US 2003/0180957 A1 (Koopman et al., "Target and method," Sep. 25, 2003) and U.S. patent publication US 2003/0173513 A1 (Koopman et al., "Probe for mass spectrometry," Sep. 18, 2003).

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry and, in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

The summary of the invention described above is non-limiting and other features and advantages of the invention will be apparent from the following detailed description of the invention, and from the claims.

DETAILED DESCRIPTION OF THE INVENTION

I General Use of Natriuretic Peptide Fragments as Prognostic and Diagnostic Markers and Specific Fragments of BNP Increased blood levels of natriuretic peptides have been found in certain disease states, suggesting a role in the pathophysiology of those diseases, including stroke, congestive heart failure (CHF), cardiac ischemia, systemic hypertension, and acute myocardial infarction. See, e.g., WO 02/089657; WO 02/083913; WO 03/016910; Hunt et al., *Biochem. Biophys. Res. Comm.* 214: 1175-83 (1995); Venugopal, *J. Clin. Pharm. Ther.* 26: 15-31, 2001; and Kalra et al., *Circulation* 107: 571-3, 2003; each of which is hereby incorporated in its entirety, including all tables, figures, and claims. The natriuretic peptides, alone, collectively, and/or together with additional proteins, can also serve as disease markers and indicators of prognosis in various cardiovascular conditions.

It has been reported that removal of natriuretic peptides from the circulation involves degradation pathways. Indeed, inhibitors of neutral endopeptidase, which cleaves natriuretic peptides under certain circumstances, have been suggested to hold promise in treatment of certain cardiovascular diseases. See, e.g., Trindade and Rouleau, *Heart Fail. Monit.* 2: 2-7, 2001. However, the measurement of the natriuretic peptides in clinical samples has focused generally upon measurement of the mature BNP, ANP, and/or CNP; their precursor molecules (i.e., pro-BNP, pro-ANP, and pro-CNP); and the fragments resulting from cleavage of the pro-form to provide the mature natriuretic peptides. The present invention describes for the first time a number of fragments produced by degradation of these molecules in biological samples. Although described hereinafter mainly with reference to BNP fragments, the general concepts described herein apply equally to ANP- and CNP-related fragments.

The failure to consider the degradation fragments that may be present in a clinical sample when measuring one or more of the natriuretic peptides may have serious consequences for the accuracy of any diagnostic or prognostic method. Consider for example a simple case, where a sandwich immunoassay is provided for BNP, and all of the BNP present has been degraded into two fragments, one of which contains the epitope corresponding to the solid phase antibody, the other of which contains the epitope corresponding to the antibody conjugate used for signal generation in the immunoassay. Because no BNP fragments present contain both epitopes, no signal will be obtained from the immunoassay, thus leading to the incorrect assumption that no BNP was originally present in the sample.

Similarly, another simple case may be considered. In a competitive assay, in which BNP present in solution competes with labeled BNP for binding to a solid phase antibody, consider that the solid phase is configured with a polyclonal antibody that would recognize both of the foregoing fragments. Each would bind to the antibody solid phase, and compete with the labeled BNP for binding. Such a situation may lead to the incorrect assumption that twice the BNP concentration actually present in the sample is detected. As described herein, the situation may actually be much more complicated than these simple situations. Because production of such fragments is an ongoing process that may be a function of, inter alia, the elapsed time between onset of an event triggering natriuretic peptide release into the tissues and the time the sample is obtained or analyzed; the elapsed time between sample acquisition and the time the sample is analyzed; the type of tissue sample at issue; the storage conditions; the quantity of proteolytic enzymes present; etc. may affect the extent of the errors in measurement.

The previously known BNP polypeptides, pre-pro-BNP, pro-BNP (BNP1-108), pro-fragment ( BNP1-76), and mature BNP (BNP77-108), contains multiple sites for possible amino acid modifications and endoproteolytic cleavage. The following new fragments have been observed BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106. FIG. 1 shows BNP77-108. Preferred degradation fragments identified in human serum or plasma include: BNP77-106, BNP79-106, BNP76-107, BNP69-108, BNP79-108, BNP80-108, BNP81-108, BNP83-108, BNP39-86, BNP53-85, BNP66-98, BNP30-103, BNP11-107, BNP9-106, and BNP3-108. BNP80-108, BNP30-106, BNP86-108, BNP77-107, BNP77-106, BNP77-103, BNP1-13, and BNP62-76 are excluded in their individually purified forms in certain embodiments of the invention. Methionine residues in fragments containing such amino acids may become oxidized, further complicating the degradation pattern.

The mass-to-charge ratios of certain BNP fragments are as follows M3464 Da—BNP77-108, M3280 Da—BNP79-108, M3170.8 Da—BNP77-106, M5377.3 Da—BNP39-86, M3660 Da—BNP53-85, M3674.4 Da—BNP66-98, M8215.5 Da—BNP30-103, M10875.5 Da—BNP11-107, M10877.4 Da—BNP9-106. The mass-to-charge ratios were determined from mass spectra generated on a Ciphergen Biosystems, Inc. PBS II mass spectrometer. This instrument has a mass accuracy of about ±-0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

Failure to consider the above-disclosed BNP fragments, including forms in which methionine residues are oxidized, can results in an incorrect estimate of the amount of BNP present and may be discarding useful information for use in diagnosis or prognosis. As discussed above, production of such fragments is an ongoing process that may be a function of, inter alia, the elapsed time between onset of an event triggering natriuretic peptide release into the tissues and the time the sample is obtained or analyzed; the elapsed time between sample acquisition and the time the sample is analyzed; the type of tissue sample at issue; the storage conditions; the quantity of proteolytic enzymes present; etc. Determination of the relative pattern of degradation may be indicative of time of adverse event; the success (or lack thereof) in treatment with protease inhibitors; whether sample storage has been adequate, etc. Moreover, the individual fragments may also find use as markers in marker panels, with or without additional markers unrelated to natriuretic peptides. Additional unrelated markers include those in WO 02/089657; WO 02/083913; and WO 03/016910, each of which is hereby incorporated in their entirety, including all tables figured and claims.

The methods described herein are applicable generally to polypeptides, and the analysis of the natriuretic peptides described in detail herein is merely exemplary. Other suitable polypeptides that may be the subject of similar analysis include angiotensin I, angiotensin II, vasopressin, calcitonin, calcitonin gene related peptide, urodilatin, urotensin II, free cardiac troponin I, free cardiac troponin T, cardiac troponin I in a complex comprising one or both of troponin T and troponin C, cardiac troponin T in a complex comprising one or both of troponin I and troponin C, total cardiac troponin I, total cardiac troponin T, pulmonary surfactant protein D, D-dimer, annexin V, enolase, creatine kinase, glycogen phosphorylase, heart-type fatty acid binding protein, phosphoglyceric acid mutase, S-100, S-100ao, plasmin-α2-antiplasmin complex, β-thromboglobulin, platelet factor 4, fibrinopeptide A, platelet-derived growth factor, prothrombin fragment 1+2, P-selectin, thrombin-antithrombin III complex, von Willebrand factor, tissue factor, thrombus precursor protein, human neutrophil elastase, inducible nitric oxide synthase, lysophosphatidic acid, malondialdehyde-modified low density lipoprotein, matrix metalloproteinase-1, matrix metalloproteinase-2, matrix metalloproteinase-3, matrix metalloproteinase-9, TIMP1, TIMP2, TIMP3, C-reactive protein, interleukin-1β, interleukin-1 receptor antagonist, interleukin-6, tumor necrosis factor α, soluble intercellular adhesion molecule-1, vascular cell adhesion molecule, monocyte chemotactic protein-1, caspase-3, human lipocalin-type prostaglandin D synthase, mast cell tryptase, eosinophil cationic protein, KL-6, procalcitonin, haptoglobin, s-CD40 ligand, S-FAS ligand, alpha 2 actin, basic calponin 1, CSRP2 elastin, LTBP4, smooth muscle myosin, smooth muscle myosin heavy chain, transgelin, aldosterone, angiotensin III, bradykinin, endothelin 1, endotehlin 2, endothelin 3, renin, APO B48, pancreatic elastase 1, pancreatic lipase, sPLA2, trypsinogen activation peptide, alpha enolase, LAMP3, phospholipase D, PLA2G5, protein D, SFTPC, defensin HBD1, defensin HBD2, CXCL-1, CXCL-2, CXCL-3, CCL2, CCL3, CCL4, CCL8, procalcitonin, protein C, serum amyloid A, s-glutathione, s-TNF P55, s-TNF P75, TAFI, TGF beta, MMP-11, brain fatty acid binding protein, CA11, CABP1, CACNA1A, CBLN1, CHN2, cleaved Tau, CRHR1, DRPLA, EGF, GPM6B, GPR7, GPR8, GRIN2C, GRM7, HAPIP, HIF 1 alpha, HIP2 KCNK4, KCNK9, KCNQ5, MAPK10, n-acetyl aspartate, NEUROD2, NRG2, PACE4, phosphoglycerate mutase, PKC gamma, prostaglandin E2, PTEN, PTPRZ1, RGS9, SCA7, secretagogin, SLC1A3, SORL1, SREB3, STAC, STX1A, STXBP1, BDNF, cystatin C, neurokinin A, substance P, interleukin-1, interleukin-11, interleukin-13, interleukin-18, interleukin-4, and interleukin-10.

The methods described herein are also applicable generally to identifying polypeptides, whether or not they are proteolytic fragments of another, larger, polypeptide, that share the ability to bind to an antibody of interest. Taking a known example, the polypeptide hormone cardiodilatin has a sequence that is identical to a portion of pro-ANP. Antibodies that bind to pro-ANP may, therefore, crossreact with cardiodilatin. If cardiodilatin was unknown in blood samples, this crossreactivity can be exploited to identify its presence by identifying those additional polypeptides that bind to the antibody.

Once unpredicted polypeptides that share the ability to bind to an antibody of interest are identified, their presence in serum may be characterized for use as disease markers as described hereinafter. In addition, antibodies may be selected to distinguish the various polypeptides. Returning to the caridodilatin/pro-ANP example above, if assays for pro-ANP had been shown to be related to a particular disease state, it may be that cardiodilatin was contributing to that relationship, or, in the alternative, confounding that relationship. Further characterization would now be possible, based on the knowledge that the antibody of interest was binding to more than the expected pro-ANP polypeptide.

II Selection of Antibodies to Natriuretic Peptide Fragments

The generation and selection of antibodies that recognize one or more natriuretic peptide fragments may be accomplished several ways. For example, one way is to purify the fragments of interest or to synthesize the fragments of interest using, e.g., solid phase peptide synthesis methods well known in the art. See, e.g., *Guide to Protein Purification,* Murray P. Deutcher, ed., *Meth. Enzymol.* Vol 182 (1990); Solid Phase Peptide Synthesis, Greg B. Fields ed., *Meth. Enzymol.* Vol 289 (1997). Regions that are common to a set of peptides may be used, rather than the entire fragment(s) of interest, to generate and/or identify antibodies that recognize the set of fragments containing that common region. Similarly, regions that are not in common between one or a set of fragment(s) may be used to generate and/or identify antibodies that distinguish between sets of fragments.

The selected polypeptides may then be injected, for example, into mice or rabbits, to generate polyclonal or monoclonal antibodies. Many procedures are available for the production of antibodies, for example, as described in Antibodies, A Laboratory Manual, Ed Harlow and David Lane, Cold Spring Harbor Laboratory (1988), Cold Spring Harbor, N.Y. Binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No.

5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified natriuretic fragments of interest and, if required, comparing the results to the affinity and specificity of the antibodies with natriuretic fragments that are desired to be excluded from binding. The screening procedure can involve immobilization of the purified natriuretic fragments in separate wells of microtiter plates. The solution containing a potential antibody or groups of antibodies is then placed into the respective microtiter wells and incubated for about 30 min to 2 h. If an antibody to the fragment(s) of interest is present in the solution, it will bind to the immobilized natriuretic fragment(s). The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized natriuretic fragment(s) is present.

The antibodies so identified may then be further analyzed for affinity and specificity to the natriuretic fragment(s) of interest in the assay design selected. In the development of immunoassays for a target protein, the purified target protein acts as a standard with which to judge the sensitivity and specificity of the immunoassay using the antibodies that have been selected. Because the binding affinity of various antibodies for the various fragments may differ; certain antibody pairs (e.g., in sandwich assays) may interfere with one another sterically, etc., assay performance of an antibody may be a more important measure than absolute affinity and specificity of an antibody.

In another preferred embodiment, antibodies or binding fragments are directed to epitopes which are not changed by oxidation of methionine residues, or that can distinguish oxidized from reduced forms. The various oxidized and reduced forms of the polypeptides can be for generating and/or identifying antibodies as discussed above.

Once antibodies to various regions of the natriuretic peptides have been obtained, these antibodies can be used to capture fragments from test samples for further characterization in order to identify the sequence of the various peptides present. Individual peptides may be obtained and sequenced using microsequencing methods known to the skilled artisan. See, e.g., *A Practical Guide to Protein and Peptide Purification for Microsequencing,* Paul T. Matsudaira, ed., Academic Press, San Diego, 1989. Peptide mass fingerprinting and amino acid analysis using mass spectrometry techniques are particularly well suited to identifying peptides so obtained. See, e.g., Westermeier and Naven, *Proteomics in Practice: A Laboratory Manual of Proteome Analysis,* Wiley-VCH Verlag-GmbH, Weinheim, 2002.

Many approaches can be taken in producing antibodies or binding fragments and screening and selecting for affinity and specificity for the various natriuretic peptide fragments, but these approaches do not change the scope of the invention.

III Qualifying Reagents for Immunoassays

A. Qualifying Antibodies

Immunoassays typically involve the use an immunoassay reagent that comprises an antibody directed against the target analyte. The accuracy of such assays depends upon the integrity and purity of the antibody in the immunoassay reagent. The presence of contaminants in an antibody reagent can interfere with an accurate measurement of the amount of antibody in the antibody reagent. Accordingly, the present invention provides methods for determining the quality of an anti-BNP antibody used in an immunoassay reagent by specifically detecting modified forms of the antibody, e.g., degraded forms, in the reagent.

Figure 3:
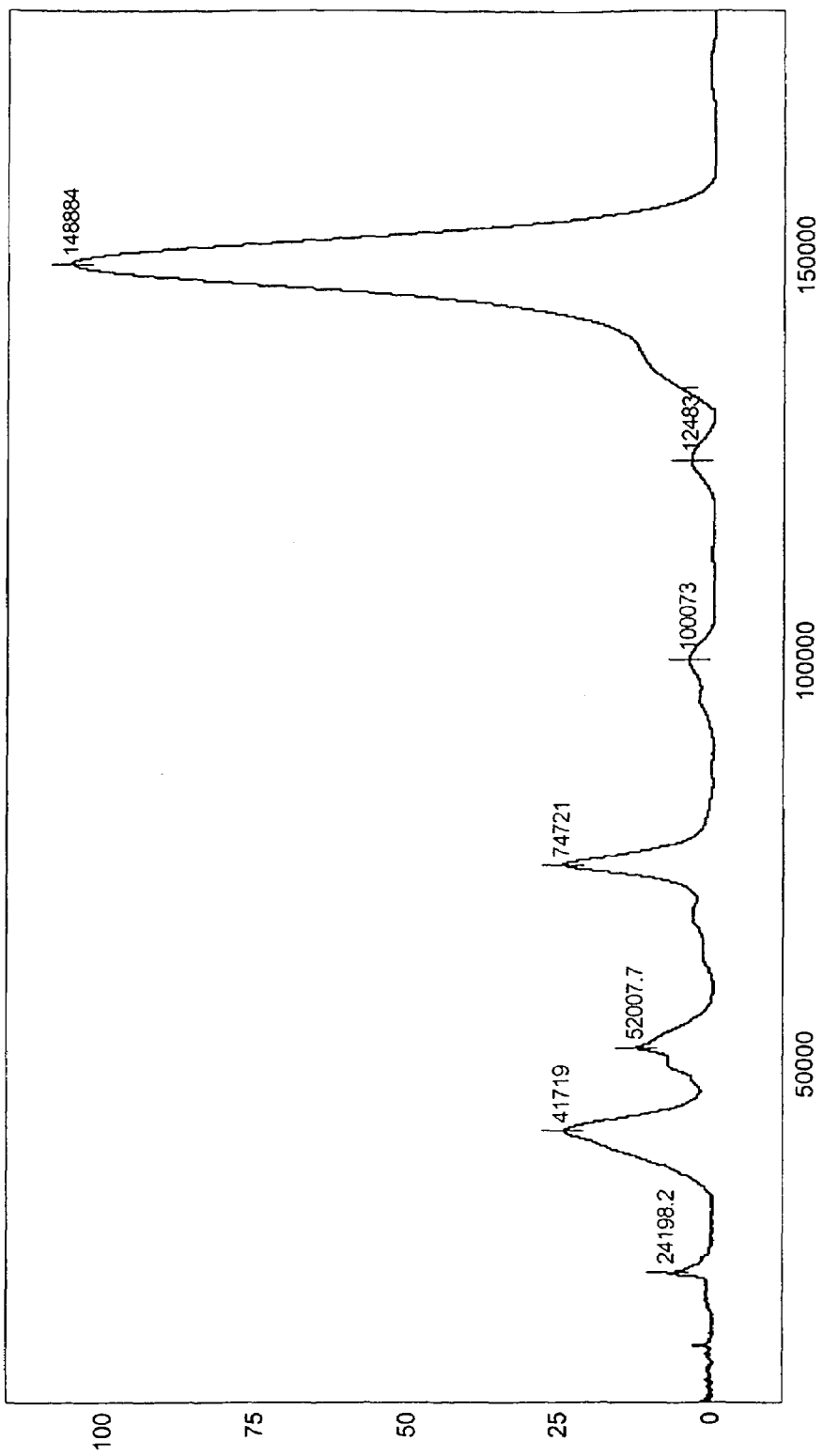
FIG. 3. Mass spectrum of antibody reagent comprising anti-BNP monoclonal also contains peaks corresponding to many proteins besides the antibody.

In one version of the method, an anti-BNP antibody used in an immunoassay, in particular a commercial immunoassay, is examined by mass spectrometry. This analysis can indicate what portion of the antibody reagent is whole and what part is degraded. For example, the immunoglobulin may be degraded into heavy chains and light chains. Also, the immunoglobulin may be degraded into fragments of the heavy and light chains. Because mass spectrometry can distinguish intact immunoglobulin and degraded versions of it based on mass differences, the immunoglobulin reagent can thereby be qualified. An exemplary mass spectrometry analysis of an antibody is shown in FIG. 3.

In another version of the method, the antibody is coupled to the surface of a SELDI probe and used to capture BNP from a sample or from a BNP calibrant for an immunoassay. This method can detect the absolute amount of intact BNP captured, as well as the relative amount of intact BNP to other molecules. The absolute quantity of an analyte as measured by an immunoassay is dependent on the quality of the reagents used to measure the analyte, as well as the quality of the reagents used to generate the standard curve (i.e. the calibrators). If the antibody is not specific for the intended analyte, it may give false elevated levels. If the calibrator is impure, the calibration curve will be inaccurate. The inaccurate quantitation of an analyte can lead to the generation of incorrect conclusions regarding the optimal cutoffs for making medical decisions and can lead to the incorrect quantitation in individuals, leading to suboptimal management.

In one aspect, this invention provides methods for characterizing and providing quality control for the antibody reagent used in an immunoassay, e.g., a tagged immunoassay. It has been found that antibody reagents used in immunoassay kits can contain contaminating proteins. These contaminants can interfere with measurements intended to quantify the actual amount of antibodies provided in an antibody reagent kit. The methods are useful for quality control in the preparation and use of antibody reagents. The methods involve measuring the amount of antibody and/or the amounts of other proteins in an antibody reagent for use in an immunoassay, e.g., in a tagged immunoassay kit. The antibody can be qualified both in terms the amount of the antibody and its quality, e.g., its state of degradation. Reagents that do not pass quality control standards for any qualifier of interest can be discarded or modified to come into compliance. Instructions for use of the reagent can take into consideration the quality of the reagent and the impact of this quality on the immunoassay. For example, one generally wants to use enough antibody reagent to capture all the target protein of interest in a sample, Therefore, the amount of antibody included in an antibody reagent can be determined with reference to the amount measured by mass spectrometry, e.g., SELDI compared with, e.g., total protein.

In immunoassays, the antibody reagent may recognize an epitope that exists not only in the target protein, but in degradation fragments of the target protein as well. For example, anti-BNP antibodies can recognize not only BNP77-108 but degradation fragments as well. Traditional tagged immunoassays that employ such antibody reagents cannot distinguish between the various forms of the target protein.

The antibody reagent in an immunoassay may not distinguish between a target polypeptide and degraded forms of a target polypeptide. Insofar as only one or some of these detected polypeptides may be responsible for the sensitivity and specificity of a diagnostic or other assay based on this detection, the detection of other polypeptides can impair sensitivity and specificity. Therefore, one may improve the assay by determining what other polypeptides are captured by the antibody reagent, and directing the assay to the detection, or use of specific polypeptides. In one embodiment, this may involve performing the assay as a sandwich assay in which the labeled antibody detects the isoform specified. Alternatively, the immunoassay may be a SELDI MS immunoassay. An immunoassay based on mass spectrometry automatically provides discrimination of the various captured polypeptides based on mass.

Kits can include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media can include addresses to internet sites that provide such instructional materials.

B. Calibrators

Calibration of an immunoassay is important for ensuring the quality of results generated in the immunoassay. Calibration generally involves the use of an immunoassay calibrator that contains the target analyte in a prescribed amount or concentration. The signal produced by the calibrator in an immunoassay is correlated to the amount of target analyte in the calibrator. This calibration, in turn, is used to correlate the amount of signal measured in a test sample with an amount of target analyte in the test sample. However, the signal generated by the calibrator may not represent the true amount of analyte in the calibrator if, for example, the target analyte in the calibrator is degraded or otherwise modified so as to corrupt the signal.

Furthermore, calibrators used in standard immunoassays may comprise not only full length calibrator protein, but degradation products, as well. This means that the calibrator may lead to mis-measurement of the amount of target in a sample. In fact, examination of a calibrant used for BNP immunoassays demonstrated that the calibrant contained not only full length BNP, but various degradation fragments of BNP, identifiable because their molecular weight corresponded to the molecular weight of identifiable sub-sequences of the BNP amino acid sequence.

Accordingly, this invention provides methods for determining the quality of a BNP immunoassay calibrator. The method involves capturing molecules from a immunoassay calibrator used in an immunoassay against BNP with an antibody that captures BNP and specifically measuring the amount of BNP polypeptide(s) captured by the antibody. Alternatively, the immunoassay could be directed to measuring a particular fragment of BNP and involve the use of antibodies against this form and a calibrator that included this form.

The relative or absolute quantities of cardiac biomarkers and protein interactors with said biomarkers, in addition to clinical parameters such as patient signs and symptoms and electrocardiogram results, can be used for diagnosis, prognosis, and patient management purposes. For example, these results can diagnose the absence or presence of acute coronary syndrome as well as the specific class of acute coronary syndrome (e.g. unstable angina versus recent myocardial infarction); determine the likely outcome of the patient in the absence of therapy (i.e. determine prognosis), and determine whether the patient is likely to benefit from a course of specific medical therapy (e.g. clotting inhibitors versus statins).

Figure 4B:
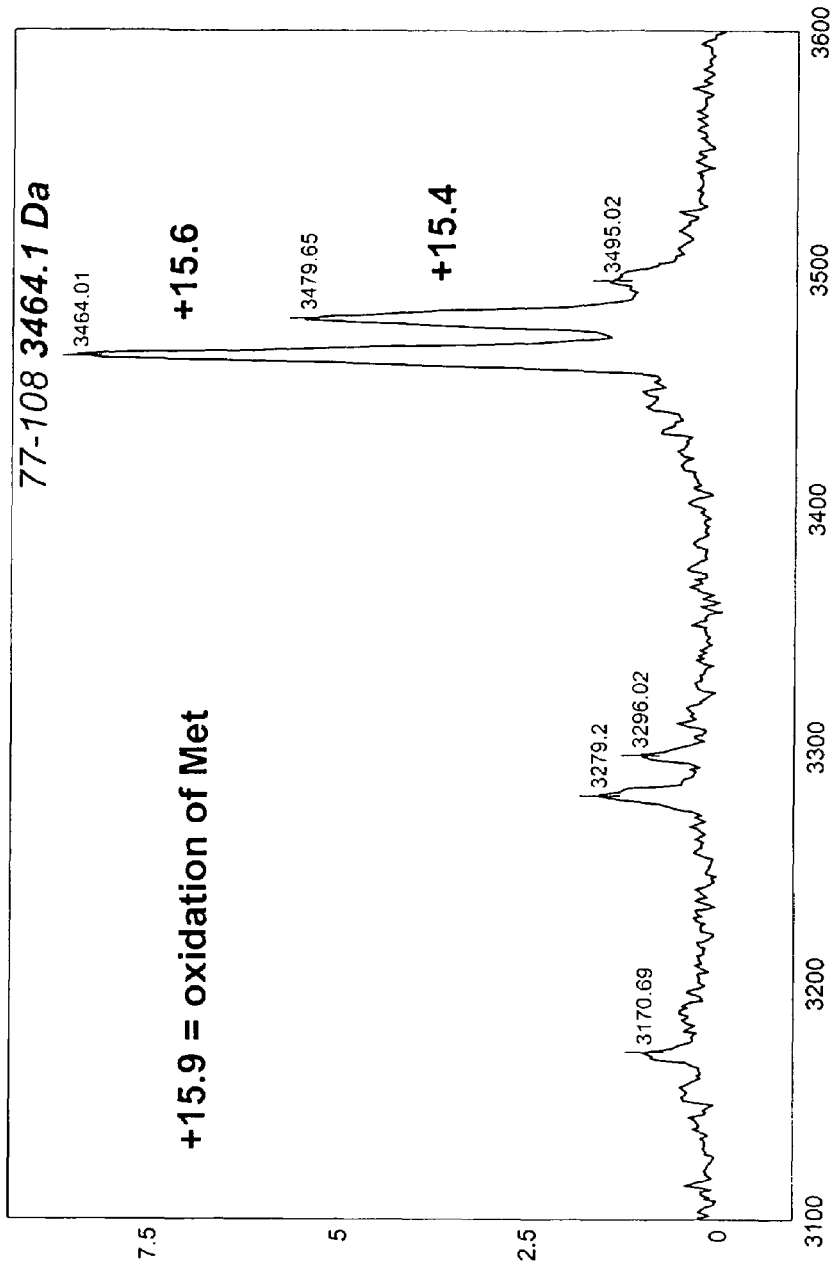
FIGS. 4A, B, C, and D. Mass spectra of proteins from a BNP calibrator solution captured by SELDI immunoassay. Proteins from the calibrator were spiked into human plasma. Anti-BNP was used to capture the proteins. Besides the 77-108 isoform at 6461, peaks are detected whose molecular weights correspond to BNP peptide fragments: A BNP isoform that weighs about 3170.8 Da and corresponds to amino acids 77 to 106 of proBNP; a BNP isoform that weighs about 3280 Da and corresponds to amino acid 79 to 108 of proBNP; a BNP isoform that weighs about 3671 Da and corresponds to amino acid 53-85 (3669) or 66-98 (3674.4) of proBNP; a BNP isoform that weighs about 8215.5 Da and corresponds to amino acids 30 to 103 of proBNP; a BNP isoform that weighs about 10875.3 and corresponds to 11-107 (108755.) or 9-106 (10874.4)of proBNP.
Figure 4C:
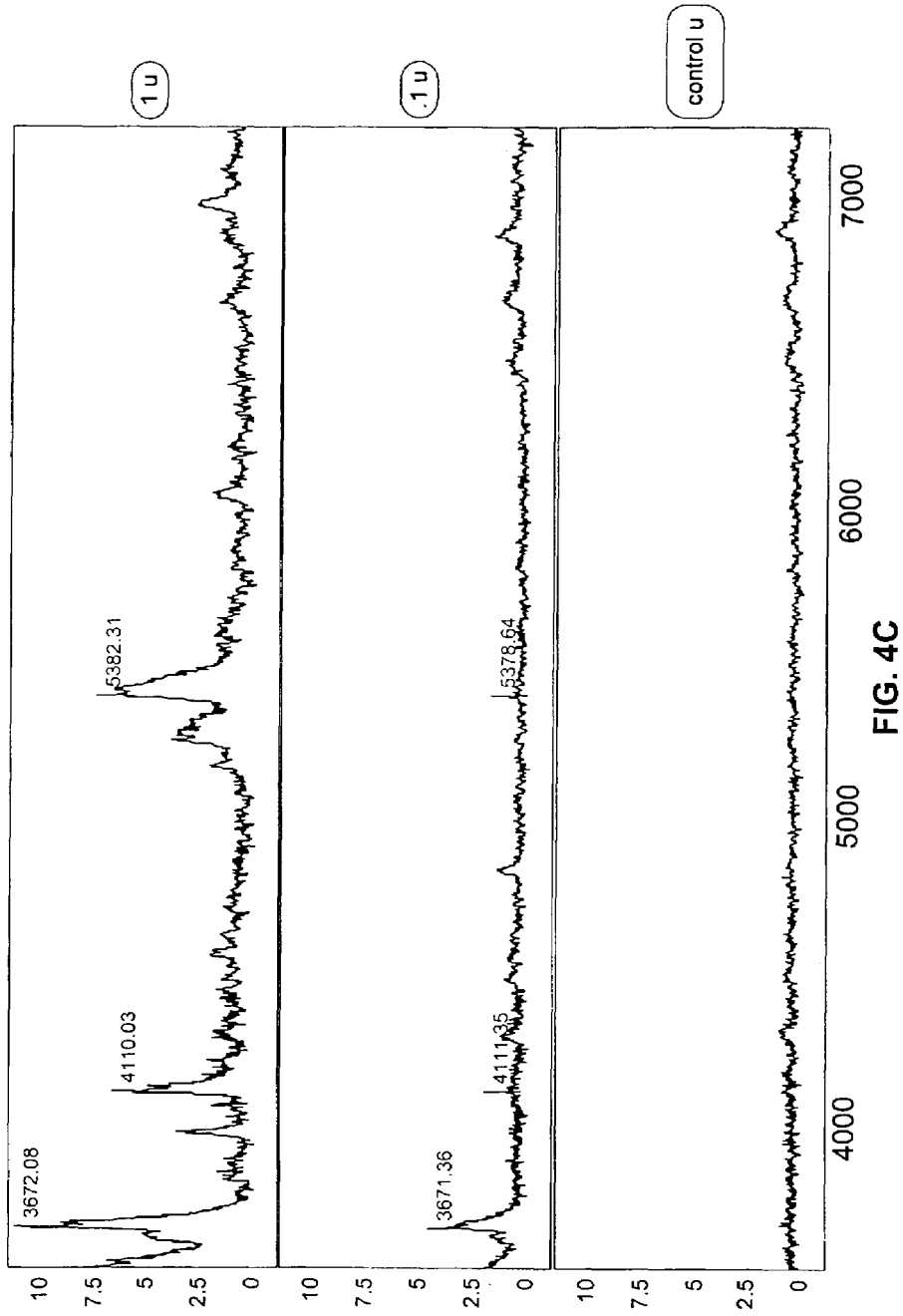
Figure 4D:
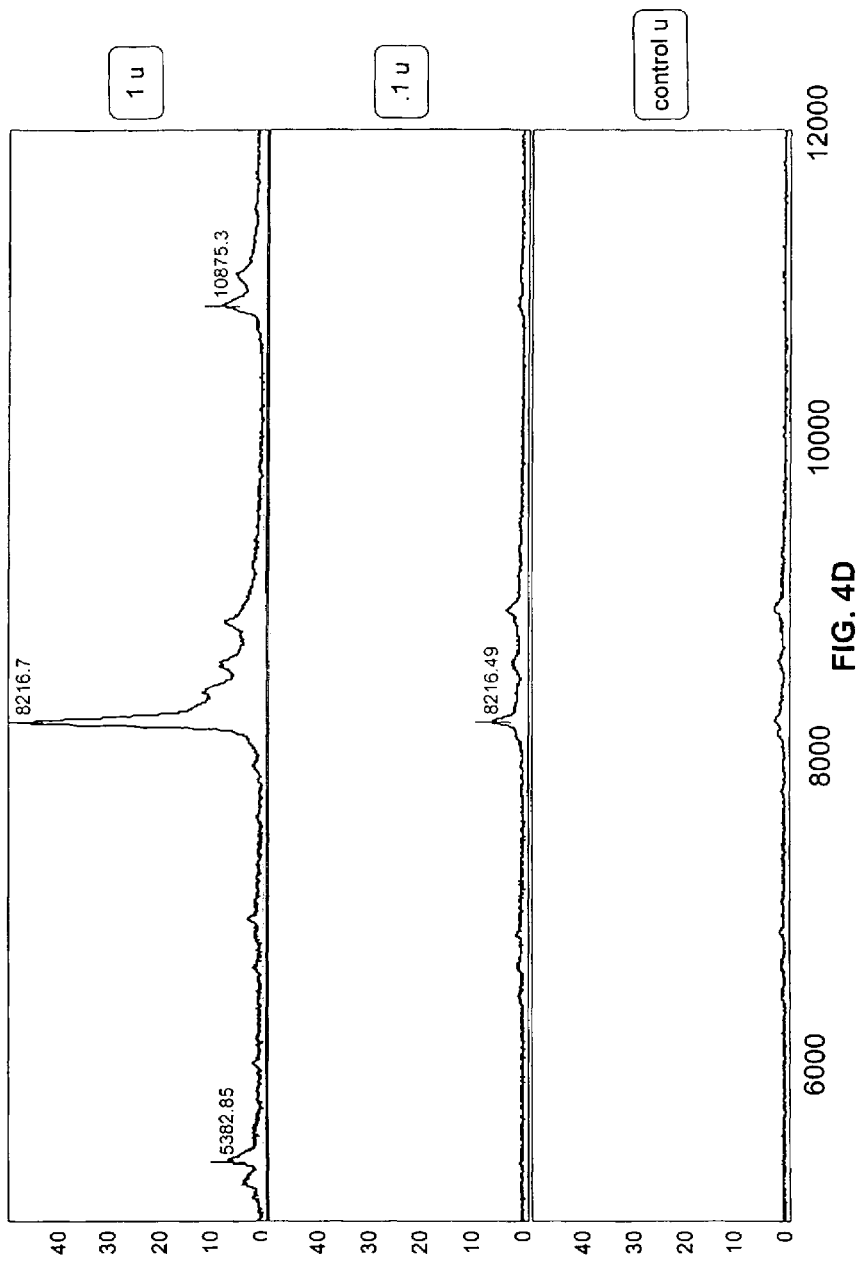
Figure 5B:
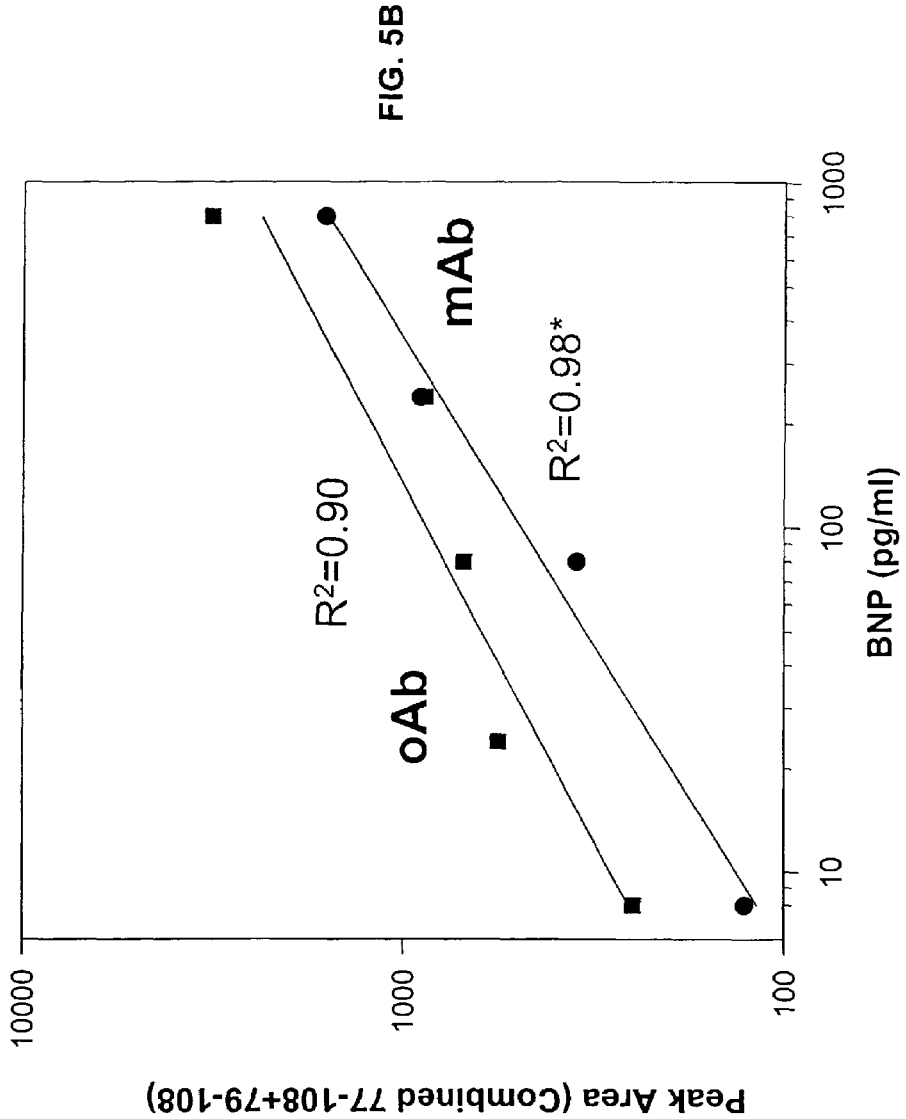
FIGS. 5A and B. Mass spectra and standard curve of BNP calibrator at various levels of concentration. Spectra show that the calibrator contains as much BNP79-108 isoform as BNP77-108 isoform.
Figure 6A:
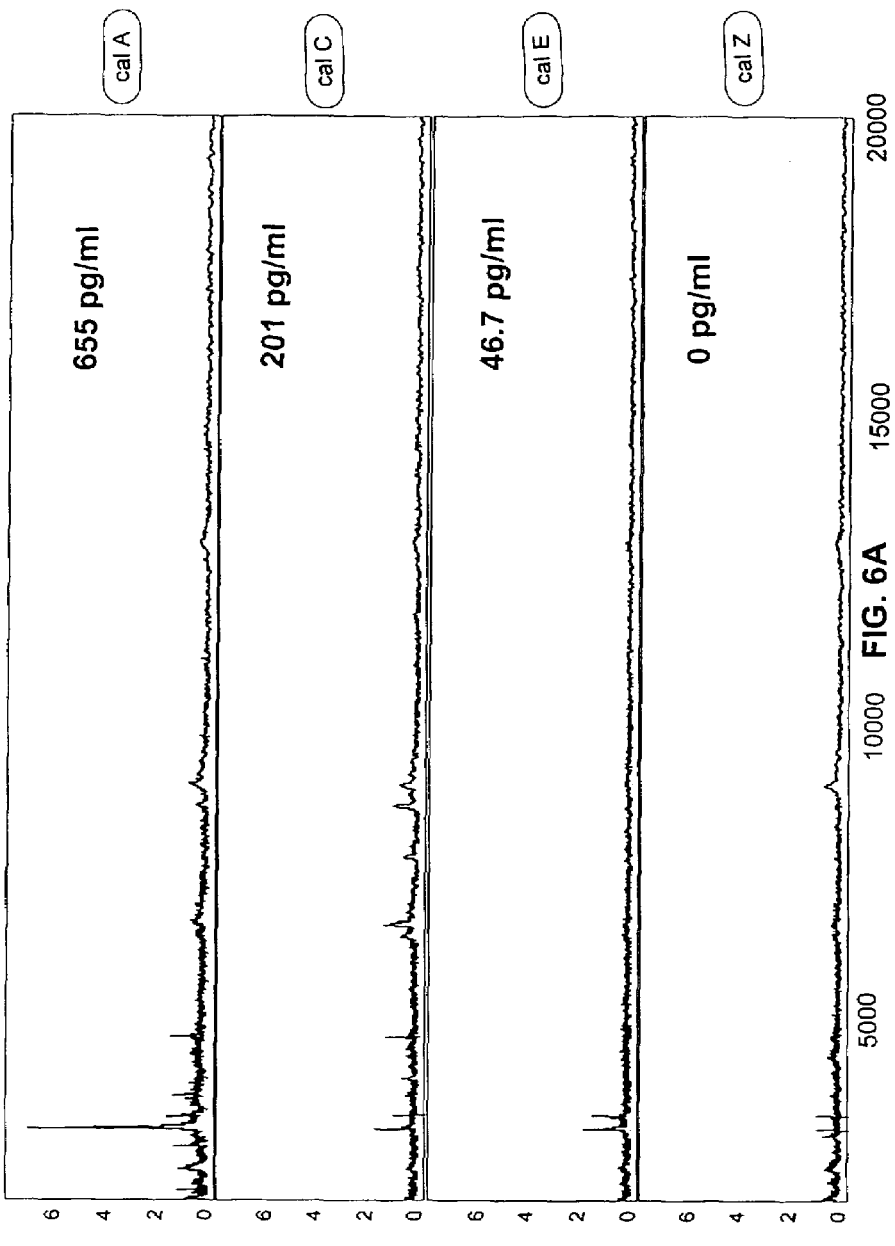
FIGS. 6A, B and C. Mass spectra and standard curve of BNP calibrator at various levels of concentration. BNP77-108 is hardly visible. When the standard is calibrated to the amount of protein corresponding to BNP79-106, BNP79-108 and a peak corresponding to either BNP69-100 or BNP76-107 the standard curve is skewed to the right, implying that a test measurement contains more BNP that the original calibrator key indicated.

Accordingly, in one aspect this invention provides a method for providing quality control in the manufacture and use of immunoassay calibrators in general and BNP immunoassay calibrators in particular. In one embodiment, the method involves qualifying the peptides in an immunoassay calibrator, e.g., a BNP immunoassay calibrator, by mass spectrometry, in particular by SELDI. This method allows more precise discrimination of those peptides, as they can be both discriminated according to mass and quantified based on the area under a mass spectrum peak. According to the method, an immunoassay calibrator solution is characterized by mass spectrometry, in particular by SELDI. The differentiation and quantitation of the peptides is performed by mass spectrometry. In one version, the peptides are captured on an SELDI MS probe, such as a probe with a hydrophobic surface or a reactive probe derivatized with an antibody that specifically recognizes polypeptides with an epitope of the calibrator polypeptide. In particular the polypeptides in the calibrator can be captured on a probe derivatized with antibody reagent used in the immunoassay kit. One may then calibrate the assay based on one or more of the peaks of interest. For example, the polypeptide can be measured as function of total protein in the calibrator. Examples SELDI analyses of calibrators are shown in FIGS. 4A, B, C and D, FIGS. 5A, and B, and FIGS. 6A, B and C.

For example, in a BNP assay, the assay can be calibrated against BNP77-108. In the case of a BNP assay, mass spectra showed that the calibrator in plasma contained many degraded forms of BNP. This implies the presence of proteases. Accordingly, one can stabilize the BNP polypeptide in the calibrator by adding one or more protease inhibitors.

In the case of BNP, while such immunoassays are directed to full length BNP, they detect other forms of BNP also. However, the general target of these immunoassays is BNP77-108. Accordingly, on can perform a SELDI immunoassay in which the amount of BNP77-108 is measured. Other fragments may be specifically detected if desired. Alternatively, one can develop an antibody that is specific for BNP77-108, and employ this in a sandwich tagged immunoassay.

Accordingly, in one embodiment, this invention provides methods for qualifying at least one form of a BNP polypeptide in a sample. The method comprises first providing a SELDI probe whose surface has been derivatized with antibodies that specifically bind to an epitope of BNP, preferably mature BNP. The probe can be a probe with a reactive surface, such as those described above. Such a probe is capable of specifically capturing the forms of BNP that comprise this epitope. Then, a sample for testing, such as a subject sample in a diagnostic test, is contacted with the bound antibodies. Polypeptides that possess the epitope are captured by the bound antibodies and unbound material is washed away. An energy absorbing molecule is then associated with the bound material. This may involve application of a traditional matrix. Alternatively, if the probe is a SEND probe on which energy absorbing molecules are already bound, no external matrix is necessary. The captured molecules are then detected by mass spectrometry. Because mass spectrometry qualifies analytes by mass, polypeptides comprising the same epitope, but differing in mass may be detected, differentiated and measured. For example, the amount of BNP77-108 can be differentiated from other forms of the molecule and quantified by this SELDI immunoassay. Indeed, examination of subject samples demonstrated that the antibody reagent used in BNP tagged immunoassays bound to many other BNP fragments other than BNP77-108 as well. The present invention allows the differentiation of these species.

IV Use of Natriuretic Peptide Degradation Products in Marker Panels

A principle of diagnostic testing is the correlation of the results of a procedure (e.g. blood test, urine test, CSF, test, sputum test, tissue biopsy, radiologic examination, measurement of one or more biomarkers, and the like) with particular clinical parameters. The correlation necessarily involves a comparison between two or more groups distinguished by the clinical parameter. A clinical parameter could be, for example, presence or absence of disease, risk of disease, stage of disease, severity of disease, class of disease or response to treatment of disease. Accordingly, the diagnostician uses this correlation to determine the status of a subject with respect to the clinical parameter. That is, the diagnostician uses the results of a procedure on a subject to classify or diagnose a subject status with respect to a clinical parameter, the confidence of the diagnosis/classification being related to the classifying or splitting power of the signs or symptoms used in the test.

Biomarkers having the most diagnostic utility, such as those of this invention, show a statistical difference in different clinical parameters of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

Methods and systems for the identification of a one or more markers for the diagnosis, and in particular for the differential diagnosis, of disease have been described previously. Suitable methods for identifying markers useful for the diagnosis of disease states are described in detail in U.S. patent application Ser. No. 10/331,127, entitled METHOD AND SYSTEM FOR DISEASE DETECTION USING MARKER COMBINATIONS, filed Dec. 27, 2002, which is hereby incorporated by reference in its entirety, including all tables, figures, and claims. Univariate analysis of markers can also be performed and the data from the univariate analyses of multiple markers can be combined to form panels of markers to differentiate different disease conditions.

In developing a panel of markers useful in diagnosis, data for a number of potential markers may be obtained from a group of subjects by testing for the presence or level of certain markers. The group of subjects is divided into two sets, and preferably the first set and the second set each have an approximately equal number of subjects. The first set includes subjects who have been confirmed as having a disease or, more generally, being in a first condition state or exhibiting a first clinical parameter. For example, this first set of patients may be those that have recently had a disease incidence, or may be those having a specific type of disease. The confirmation of the condition state may be made through a more rigorous and/or expensive testing such as MRI or CT. Hereinafter, subjects in this first set will be referred to as "diseased".

The second set of subjects are simply those who do not fall within the first set and, therefore, exhibit a second clinical parameter. Subjects in this second set may be "non-diseased;" that is, normal subjects. Alternatively, subjects in this second set may be selected to exhibit one symptom or a constellation of symptoms that mimic those symptoms exhibited by the "diseased" subjects. In still another alternative, this second set may represent those at a different time point from disease incidence.

The data obtained from subjects in these sets includes levels of a plurality of markers, including for purposes of the present invention, one or more fragments of natriuretic peptides either measured individually or as a group. Preferably, data for the same set of markers is available for each patient. This set of markers may include all candidate markers which may be suspected as being relevant to the detection of a particular disease or condition. Actual known relevance is not required. Embodiments of the methods and systems described herein may be used to determine which of the candidate markers are most relevant to the diagnosis of the disease or condition. The levels of each marker in the two sets of subjects may be distributed across a broad range, e.g., as a Gaussian distribution. However, no distribution fit is required.

A marker often is incapable of definitively identifying a patient as either diseased or non-diseased. For example, if a patient is measured as having a marker level that falls within the overlapping region, the results of the test will be useless in diagnosing the patient. An artificial cutoff may be used to distinguish between a positive and a negative test result for the detection of the disease or condition. Regardless of where the cutoff is selected, the effectiveness of the single marker as a diagnosis tool is unaffected. Changing the cutoff merely trades off between the number of false positives and the number of false negatives resulting from the use of the single marker. The effectiveness of a test having such an overlap is often expressed using a ROC (Receiver Operating Characteristic) curve. ROC curves are well known in the art.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives that test as positive. Negative predictive value is the percentage of actual negatives that test as negative.

The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As discussed above, the measurement of the level of a single marker may have limited usefulness. The measurement of additional markers provides additional information, but the difficulty lies in properly combining the levels of two potentially unrelated measurements. In the methods and systems according to embodiments of the present invention, data relating to levels of various markers for the sets of diseased and non-diseased patients may be used to develop a panel of markers to provide a useful panel response. The data may be provided in a database such as Microsoft Access, Oracle, other SQL databases or simply in a data file. The database or data file may contain, for example, a patient identifier such as a name or number, the levels of the various markers present, and whether the patient is diseased or non-diseased.

Next, an artificial cutoff region may be initially selected for each marker. The location of the cutoff region may initially be selected at any point, but the selection may affect the optimization process described below. In this regard, selection near a suspected optimal location may facilitate faster convergence of the optimizer. In a preferred method, the cutoff region is initially centered about the center of the overlap region of the two sets of patients. In one embodiment, the cutoff region may simply be a cutoff point. In other embodiments, the cutoff region may have a length of greater than zero. In this regard, the cutoff region may be defined by a center value and a magnitude of length. In practice, the initial selection of the limits of the cutoff region may be determined according to a pre-selected percentile of each set of subjects. For example, a point above which a pre-selected percentile of diseased patients are measured may be used as the right (upper) end of the cutoff range.

Each marker value for each patient may then be mapped to an indicator. The indicator is assigned one value below the cutoff region and another value above the cutoff region. For example, if a marker generally has a lower value for non-diseased patients and a higher value for diseased patients, a zero indicator will be assigned to a low value for a particular marker, indicating a potentially low likelihood of a positive diagnosis. In other embodiments, the indicator may be calculated based on a polynomial. The coefficients of the polynomial may be determined based on the distributions of the marker values among the diseased and non-diseased subjects.

The relative importance of the various markers may be indicated by a weighting factor. The weighting factor may initially be assigned as a coefficient for each marker. As with the cutoff region, the initial selection of the weighting factor may be selected at any acceptable value, but the selection may affect the optimization process. In this regard, selection near a suspected optimal location may facilitate faster convergence of the optimizer. In a preferred method, acceptable weighting coefficients may range between zero and one, and an initial weighting coefficient for each marker may be assigned as 0.5. In a preferred embodiment, the initial weighting coefficient for each marker may be associated with the effectiveness of that marker by itself. For example, a ROC curve may be generated for the single marker, and the area under the ROC curve may be used as the initial weighting coefficient for that marker.

Next, a panel response may be calculated for each subject in each of the two sets. The panel response is a function of the indicators to which each marker level is mapped and the weighting coefficients for each marker. In a preferred embodiment, the panel response (R) for a each subject (j) is expressed as:

$$R_j = \Sigma w_i I_{i,j},$$

where i is the marker index, j is the subject index, $w_i$ is the weighting coefficient for marker i, I is the indicator value to which the marker level for marker i is mapped for subject j, and $\Sigma$ is the summation over all candidate markers i.

One advantage of using an indicator value rather than the marker value is that an extraordinarily high or low marker levels do not change the probability of a diagnosis of diseased or non-diseased for that particular marker. Typically, a marker value above a certain level generally indicates a certain condition state. Marker values above that level indicate the condition state with the same certainty. Thus, an extraordinarily high marker value may not indicate an extraordinarily high probability of that condition state. The use of an indicator which is constant on one side of the cutoff region eliminates this concern.

The panel response may also be a general function of several parameters including the marker levels and other factors including, for example, race and gender of the patient. Other factors contributing to the panel response may include the slope of the value of a particular marker over time. For example, a patient may be measured when first arriving at the hospital for a particular marker. The same marker may be measured again an hour later, and the level of change may be reflected in the panel response. Further, additional markers may be derived from other markers and may contribute to the value of the panel response. For example, the ratio of values of two markers may be a factor in calculating the panel response.

Having obtained panel responses for each subject in each set of subjects, the distribution of the panel responses for each set may now be analyzed. An objective function may be defined to facilitate the selection of an effective panel. The objective function should generally be indicative of the effectiveness of the panel, as may be expressed by, for example, overlap of the panel responses of the diseased set of subjects and the panel responses of the non-diseased set of subjects. In this manner, the objective function may be optimized to maximize the effectiveness of the panel by, for example, minimizing the overlap.

In a preferred embodiment, the ROC curve representing the panel responses of the two sets of subjects may be used to define the objective function. For example, the objective function may reflect the area under the ROC curve. By maximizing the area under the curve, one may maximize the effectiveness of the panel of markers. In other embodiments, other features of the ROC curve may be used to define the objective function. For example, the point at which the slope of the ROC curve is equal to one may be a useful feature. In other embodiments, the point at which the product of sensitivity and specificity is a maximum, sometimes referred to as the "knee," may be used. In an embodiment, the sensitivity at the knee may be maximized. In further embodiments, the sensitivity at a predetermined specificity level may be used to define the objective function. Other embodiments may use the specificity at a predetermined sensitivity level may be used. In still other embodiments, combinations of two or more of these ROC-curve features may be used.

It is possible that one of the markers in the panel is specific to the disease or condition being diagnosed. When such markers are present at above or below a certain threshold, the panel response may be set to return a "positive" test result. When the threshold is not satisfied, however, the levels of the marker may nevertheless be used as possible contributors to the objective function.

An optimization algorithm may be used to maximize or minimize the objective function. Optimization algorithms are well-known in the art and include several commonly available minimizing or maximizing functions including the Simplex method and other constrained optimization techniques. Some minimization functions are better than others at searching for global minimums, rather than local minimums. In the optimization process, the location and size of the cutoff region for each marker may be allowed to vary to provide at least two degrees of freedom per marker. Such variable parameters are referred to herein as independent variables. In a preferred embodiment, the weighting coefficient for each marker is also allowed to vary across iterations of the optimization algorithm. In various embodiments, any permutation of these parameters may be used as independent variables.

In addition to the above-described parameters, the sense of each marker may also be used as an independent variable. For example, in many cases, it may not be known whether a higher level for a certain marker is generally indicative of a diseased state or a non-diseased state. In such a case, it may be useful to allow the optimization process to search on both sides. In practice, this may be implemented in several ways. For example, in one embodiment, the sense may be a truly separate independent variable which may be flipped between positive and negative by the optimization process. Alternatively, the sense may be implemented by allowing the weighting coefficient to be negative.

The optimization algorithm may be provided with certain constraints as well. For example, the resulting ROC curve may be constrained to provide an area-under-curve of greater than a particular value. ROC curves having an area under the curve of 0.5 indicate complete randomness, while an area under the curve of 1.0 reflects perfect separation of the two sets. Thus, a minimum acceptable value, such as 0.75, may be used as a constraint, particularly if the objective function does not incorporate the area under the curve. Other constraints may include limitations on the weighting coefficients of particular markers. Additional constraints may limit the sum of all the weighting coefficients to a particular value, such as 1.0.

The iterations of the optimization algorithm generally vary the independent parameters to satisfy the constraints while minimizing or maximizing the objective function. The number of iterations may be limited in the optimization process. Further, the optimization process may be terminated when the difference in the objective function between two consecutive iterations is below a predetermined threshold, thereby indicating that the optimization algorithm has reached a region of a local minimum or a maximum.

Thus, the optimization process may provide a panel of markers including weighting coefficients for each marker and cutoff regions for the mapping of marker values to indicators. In order to develop lower-cost panels which require the measurement of fewer marker levels, certain markers may be eliminated from the panel. In this regard, the effective contribution of each marker in the panel may be determined to identify the relative importance of the markers. In one embodiment, the weighting coefficients resulting from the optimization process may be used to determine the relative importance of each marker. The markers with the lowest coefficients may be eliminated.

In certain cases, the lower weighting coefficients may not be indicative of a low importance. Similarly, a higher weighting coefficient may not be indicative of a high importance. For example, the optimization process may result in a high coefficient if the associated marker is irrelevant to the diagnosis. In this instance, there may not be any advantage that will drive the coefficient lower. Varying this coefficient may not affect the value of the objective function.

V Use of BNP and its Fragments for Determining a Clinical Status of Patients and a Treatment Regimen A useful diagnostic or prognostic indicator, such as the natriuretic peptide fragments described herein, can help clinicians select between alternative therapeutic regimens. For example, patients with elevation in cardiac troponin T or I following an acute coronary syndrome appear to derive specific benefit from an early aggressive strategy that includes potent antiplatelet and antithrombotic therapy, and early revascularization. Hamm et al., *N. Engl. J. Med.* 340: 1623-9 (1999); Morrow et al., *J. Am. Coll. Cardiol.* 36: 1812-7 (2000); Cannon et al., *Am. J. Cardiol.* 82: 731-6 (1998). Additionally, patients with elevation in C-reactive protein following myocardial infarction appear to derive particular benefit from HMG-CoA Reductase Inhibitor therapy. Ridker et al., *Circulation* 98: 839-44 (1998). Among patients with congestive heart failure, pilot studies suggest that ACE inhibitors may reduce BNP levels in a dose dependent manner. Van Veldhuisen et al., *J. Am. Coll. Cardiol.* 32: 1811-8 (1998).

In the present case, elevated levels of BNP correlate with heart disease, more particularly cardiac tissue damage and acute cardiac syndrome. The diagnostician can use a measurement of BNP to determine the heart disease status of a subject. For example, a doctor can use the amount of BNP in a patient blood sample to diagnose the presence or absence of acute coronary syndrome. The phrase "acute coronary syndrome status" includes distinguishing, inter alia, acute coronary syndrome v. non-acute coronary syndrome.

A typical BNP immunoassay does not distinguish between BNP and fragments of BNP captured by the antibody, and also does not detect protein interactors. Therefore, the typical immunoassay results in the correlation of all BNP forms together with the clinical parameter of interest, e.g., acute coronary syndrome. However, by specifically distinguishing the measurements of BNP, its various forms and interactors, this invention allows the specific correlation of these analytes with the clinical parameter. Specific correlation of particular analytes in a sample provides greater specificity and sensitivity in diagnosis.

The following are recommended for meaningful BNP assays: They should use antibodies that recognize epitopes not affected by proteolysis; should react with post-translationally modified BNPs; should be standardized between manufacturers using internationally accepted standards when they become available; should be free of HAMA, RF, fibrin and other interferences.

Accordingly, in one aspect this invention provides diagnostic, prognostic and theranostic methods using the specific measurement of at least one biomarker selected from BNP polypeptides, including fragments, or biomolecular interactors of BNP and anti-BNP antibodies with these molecules. The methods involve first providing a specific measurement of the target form of BNP by any method, and then correlating the measurement with the clinical parameter of interest, e.g., acute coronary syndrome. By correlating the measurement, one is able to determine the subject status with respect to the particular clinical parameter in question. Based on this correlation, further procedures may be indicated, including additional diagnostic tests or therapeutic procedures or regimens. Each of the biomarkers of this invention can be individually correlated with disease.

Any form of BNP or protein interactor, individually, is useful in aiding in the determination of acute coronary syndrome status. First, the selected biomarker is specifically measured in a subject sample using the methods described herein, e.g., capture on a SELDI biochip followed by detection by mass spectrometry. Then, the measurement is compared with a diagnostic amount or cutoff that distinguishes one diagnostic parameter from another, e.g., a positive acute coronary syndrome status from a negative acute coronary syndrome status. The diagnostic amount represents a measured amount of a biomarker above which or below which a subject is classified as having a particular clinical parameter. For example, if the biomarker is up-regulated compared to normal in clinical parameter, then a measured amount above the diagnostic cutoff provides a diagnosis of clinical parameter. Alternatively, if the biomarker is down-regulated in acute coronary syndrome, then a measured amount below the diagnostic cutoff provides a diagnosis of acute coronary syndrome. As is well understood in the art, by adjusting the particular diagnostic cutoff used in an assay one can increase sensitivity or specificity of the diagnostic assay depending on the preference of the diagnostician.

In some embodiments, the mere presence or absence of a biomarker, without quantifying the amount of the biomarker, is useful and can be correlated with a probable diagnosis of acute coronary syndrome. Thus, a detected presence or absence, respectively, of these markers in a subject being tested indicates that the subject has a higher probability of having acute coronary syndrome.

While individual biomarkers are useful diagnostic markers, it has been found that a combination of biomarkers can provide greater predictive value of a particular status than single markers alone. Specifically, the detection of a plurality of markers in a sample can increase the percentage of true positive and true negative diagnoses and decreases the percentage of false positive or false negative diagnoses. Thus, in one embodiment, one measures the relative ratio of various forms of BNP polypeptides, including fragments, or BNP interactors.

In certain embodiments of the methods of determining acute coronary syndrome status, the methods further comprise managing subject treatment based on the status. Such management describes the actions of the physician or clinician subsequent to determining acute coronary syndrome status. For example, if a physician makes a diagnosis of acute coronary syndrome, then a certain regime of treatment, such as medical intervention (e.g. statins, beta blocker, glycoprotein IIb/IIIa inhibitor) or invasive intervention (e.g. revascularization) might follow. The specific complement of biomarkers and their interactors can predict the optimal course of treatment. Alternatively, a diagnosis of non-acute coronary syndrome might be followed with no treatment. If the diagnostic test gives an inconclusive result on acute coronary syndrome status, further tests may be called for.

Similarly, "tailoring" diuretic and vasodilator therapy based on the level of the various natriuretic peptide fragments may improve outcomes. See, e.g., Troughton et al., Lancet 355: 1126-30 (2000). Finally, in a single pilot study of 16 patients found that randomization to an ACE inhibitor rather than placebo following Q-wave MI was associated with reduced BNP levels over the subsequent 6-month period. Motwani et al., Lancet 341: 1109-13 (1993). Because BNP is a counter-regulatory hormone with beneficial cardiac and renal effects, it is likely that a change in BNP concentration reflects improved ventricular function and reduced ventricular wall stress. A recent article demonstrates the correlation of NT pro-BNP and BNP assays (Fischer et al., Clin. Chem. 47: 591-594 (2001). It is a further objective of this invention that the concentration of natriuretic peptide fragments, either individually or considered in groups, can be used to guide diuretic and vasodilator therapy to improve patient outcome. Additionally, the measurement of natriuretic peptide fragments, either individually or considered in groups, for use as a prognostic indicator for patients suffering from acute coronary syndromes, is within the scope of the present invention.

Recent studies in patients hospitalized with congestive heart failure suggest that serial BNP measurements may provide incremental prognostic information as compared to a single measurement; that is, assays can demonstrate an improving prognosis when BNP falls after therapy than when it remains persistently elevated. Cheng et al., J. Am. Coll. Cardiol. 37: 386-91 (2001). Thus, serial measurements of natriuretic peptide fragments may increase the prognostic and/or diagnostic value of a marker in patients, and is thus within the scope of the present invention.

VI Assay Measurement Strategies

The methods involve capturing one or more BNP polypeptides, including fragments, and/or biomolecular interactors of BNP and anti-BNP antibodies onto a solid substrate. Typically they will be captured using an antibody or other biospecific capture reagent specifically binding to a BNP polypeptide, and, in particular, an antibody used in an immunoassay. These molecules also can be captured with non-specific methods, such as chromatographic materials. The captured molecules are then specifically detected and distinguished from one another by any appropriate detection means.

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), use of biosensors or natural receptors.

Numerous methods and devices are well known for the detection and analysis of polypeptides or proteins in test samples. In preferred embodiments, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. Robotic instrumentation including but not limited to Beckman Access, Abbott AxSym, Roche ElecSys, Dade Behring Stratus systems are among the immunoassay analyzers that are capable of performing the immunoassays taught herein. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like. Any suitable immunoassay may be utilized, for example, enzyme-linked immunoassays (ELISA), radioimmunoassays (RIAs), competitive binding assays, sandwich immunoassays, mass spectroscopy immunoassays, and other types of immunoassays. Specific immunological binding of the antibody to the one or more natriuretic peptide fragments can be detected directly or indirectly. Antibodies attached to a second molecule, such as a detectable label, are referred to herein as "antibody conjugates." Natural receptors for the natriuretic peptides exist, and that these receptors may also be used in a manner akin to antibodies in providing binding assays.

The use of immobilized antibodies specific for the one or more polypeptides is also contemplated by the present invention. The antibodies can be immobilized onto a variety of solid supports, such as magnetic or chromatographic matrix particles, the surface of an assay place (such as microtiter wells), pieces of a solid substrate material or membrane (such as plastic, nylon, paper), and the like. An assay strip can be prepared by coating the antibody or a plurality of antibodies in an array on solid support. This strip can then be dipped into the test sample and then processed quickly through washes and detection steps to generate a measurable signal, such as a colored spot. Alternatively, the antibodies can be immobilized onto biochips that contain probes that can be used in mass spectroscopy methods such as SELDI.

The analysis of a plurality of polypeptides may be carried out separately or simultaneously with one test sample. For separate or sequential assay, suitable apparatuses include clinical laboratory analyzers such as the ElecSys (Roche), the AxSym (Abbott), the Access (Beckman), the ADVIA® CENTAUR® (Bayer) immunoassay systems, and the NICHOLS ADVANTAGE® (Nichols Institute) immunoassay system. Preferred apparatuses or protein chips perform simultaneous assays of a plurality of polypeptides on a single surface. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mol. Med.* 6: 329-340 (2002)) and certain capillary devices (see, e.g., U.S. Pat. No. 6,019,944), and protein biochips as defined herein. In these embodiments, each discrete surface location may comprise antibodies to immobilize one or more analyte(s) (e.g., one or more polypeptides of the invention) for detection at each location. Surfaces may alternatively comprise one or more discrete particles (e.g., microparticles or nanoparticles) immobilized at discrete locations of a surface, where the microparticles comprise antibodies to immobilize one analyte (e.g., one or more polypeptides of the invention) for detection. Alternatively, polypeptides can be analyzed using a mass spectrometer such as a PBSII mass spectrometer (Ciphergen).

Often multiple samples (for example, at successive time points) are tested from the same individual. Such testing of serial samples will allow the identification of changes in polypeptide levels over time. Increases or decreases in polypeptide levels, as well as the absence of change in such levels, provide useful information about the disease status that includes, but is not limited to identifying the approximate time from onset of the event, the presence and amount of salvageable tissue, the appropriateness of drug therapies, the effectiveness of various therapies as indicated by reperfusion or resolution of symptoms, differentiation of the various types of disease having similar symptoms, identification of the severity of the event, identification of the disease severity, and identification of the patient's outcome, including risk of future events.

A panel consisting of the polypeptides referenced above, and optionally including other protein markers useful in diagnosis, prognosis, or differentiation of disease, may be constructed to provide relevant information related to differential diagnosis. Such a panel may be constructed to detect 1, 2, 3, 4, 5, 6, 7, 8, 9, 10, 15, 20, or more or individual analytes, including one or more polypeptides of the present invention. The analysis of a single analyte or subsets of analytes can be carried out to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, a single analyte or a subset of analytes can be used in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W. B. Saunders and Company, p. 496).

The analysis of analytes can be carried out in a variety of physical formats as well. For example, the use of microtiter plates or automation can be used to facilitate the processing of large numbers of test samples. Alternatively, single sample formats can be developed to facilitate immediate treatment and diagnosis in a timely fashion, for example, in ambulatory transport or emergency room settings.

As discussed above, samples may continue to degrade the natriuretic peptides or fragments thereof, even once the sample is obtained. Thus, it may be advantageous to add one or more protease inhibitors to samples prior to assay. Numerous protease inhibitors are known to those of skill in the art, and exemplary inhibitors may be found in, e.g., The Complete Guide for Protease Inhibition, Roche Molecular Biochemicals, updated Jun. 3, 1999 at http://www.roche-applied science.com/fst/products.htm?/prod_inf/manuals/protease/prot_toc.htm, which is hereby incorporated in its entirety. Because various metalloproteases and calcium-dependent proteases are known to exist in blood-derived samples, chelators such as EGTA and/or EDTA, also act as protease inhibitors.

VII Natriuretic Peptide Fragment and Interactor Detection Using Mass Spectrometry

A. General

Mass spectrometry provides a means to specifically detect different forms of a protein and protein interactors in a sample. In mass spectrometry analytes are separated by mass and can be distinguished based on their mass signature. Thus, fragments of a protein can be distinguished from a full-length protein. Furthermore, the mass also can indicate the particular location of the fragment within the protein. Other forms of protein decoration, such as phosphorylation, also provide specific mass signatures that can be identified.

The use of affinity mass spectrometry provides an immunoassay in which a target analyte, its modified forms, and biomolecules that interact with these proteins or the antibody all can be specifically distinguished and measured. Affinity mass spectrometry is a method in which analytes are captured onto a solid surface with an affinity reagent, such as an antibody, another biospecific capture reagent or a chromatographic adsorbent, and detected by mass spectrometry through, e.g., laser desorption/ionization from the surface with subsequent detection and differentiation by mass spectrometry.

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

Biospecific adsorbents include those molecules that bind a target analyte with an affinity of at least $10^{-9}$ M, $10^{-10}$ M, $10^{-11}$ M or $10^{-12}$ M. Biospecific capture reagents include antibodies, binding fragments of antibodies (e.g., single chain antibodies, Fab' fragments, F(ab)'2 fragments, and scFv proteins and affibodies (Affibody, Teknikringen 30, floor 6, Box 700 04, Stockholm SE-10044, Sweden, U.S. Pat. No. 5,831,012)) and any other molecule that specifically binds to a BNP polypeptide. Depending on intended use, they also may include receptors and other proteins that specifically bind another biomolecule. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

B. SELDI

1. Sample Preparation

A preferred protocol for the detection of the biomarkers of this invention is as follows. The biological sample to be tested as used herein is a sample of biological tissue or fluid and includes human and animal body fluid such as whole blood, plasma, white blood cells, cerebrospinal fluid, urine, semen, vaginal secretions, lymphatic fluid, and various external secretions of the respiratory, intestinal and genitourinary tracts, tears, saliva, milk, ductal lavage, seminal plasma, tissue biopsy, fixed tissue specimens, fixed cell specimens, cell extracts and cell culture supernatents and derivatives of these, e.g., blood or a blood derivative such as serum, preferably is subject to pre-fractionation before SELDI analysis. This simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4Various fractions containing the biomarker are collected.

The sample to be tested (preferably pre-fractionated) is then contacted with an affinity capture probe comprising an anti-BNP antibody, e.g., a pre-activated PS10 or PS20 ProteinChip array (Ciphergen Biosystems, Inc.). The probe is washed with a buffer that will retain BNP polypeptides, BNP fragments and/or biomolecular interactors of BNP and anti-BNP antibodies while washing away unbound molecules. A suitable wash for these molecules is the buffer identified in the Example. The analytes are detected by laser desorption/ionization mass spectrometry.

2. SELDI Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

VIII Discovery of Patterns of BNP Forms Correlated with Clinical Parameters Using Learning Sets While single target analytes have traditionally been used as correlates of clinical parameters, such as presence or absence of disease, scientists and physicians have taken increasing interest in the use of multiple makers. This approach has become possible as a result of new technologies, such as gene arrays and affinity mass spectrometry that allow differential detection of many different molecules in a clinical sample. The discovery of patterns of molecules that can be correlated with a clinical parameter involves the multivariate analysis of measurements of a plurality of molecules, such as proteins, in a sample.

Accordingly, in one aspect this invention provides a method for discovering patterns of proteins including BNP, BNP fragments, e.g., BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106, or biomolecules that interact with these, which patterns correlate with a clinical parameter of interest. This method involves training a learning algorithm with a learning set of data that includes measurements of the aforementioned molecules and generating a classification algorithm that can classify an unknown sample into a class represented by clinical parameter.

The method involves, first, providing a learning set of data. The learning set includes data objects. Each data object represents a subject for which clinical data has been developed. The clinical data included in the data object includes the specific measurements of BNP, modified forms of BNP and biomolecular interactors of BNP and anti-BNP antibodies with these. Each subject is classified into one of at least two different clinical parameter classes. For example, the clinical parameters could include presence or absence of disease, risk of disease, stage of disease, response to treatment of disease or class of disease.

In a preferred embodiment, the learning set will be in the form of a table in which, for example, each row is data object representing a sample. The columns contain information identifying the subject, data providing the specific measurements of each of the molecules measured and optionally identifying the clinical parameter associated with the subject.

The learning set is then used to train a classification algorithm. Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000.

In supervised classification, each data object includes data indicating the clinical parameter class to which the subject belongs. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines). A preferred supervised classification method is a recursive partitioning process. Recursive partitioning processes use recursive partitioning trees to classify spectra derived from unknown samples.

In other embodiments, the classification models that are created can be formed using unsupervised learning methods. Unsupervised classification attempts to learn classifications based on similarities in the training data set. In this case, the data representing the class to which the subject belongs is not included in the data object representing that subject, or such data is not used in the analysis. Unsupervised learning methods include cluster analyses. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. patent application 2002 0193950 A1 (Gavin et al., "Method or analyzing mass spectra"), U.S. patent application 2003 0004402 A1 (Hitt et al., "Process for discriminating between biological states based on hidden patterns from biological data"), and U.S. patent application 2003 0055615 A1 (Zhang and Zhang, "Systems and methods for processing biological expression data").

Thus trained, learning algorithm will generate a classification model that classifies a sample into one of the classification groups. The classification model usually involves a subset of all the markers included in the learning set. The classification model can be used to classify an unknown sample into one of the groups.

EXAMPLES

The following examples serve to illustrate the present invention. These examples are in no way intended to limit the scope of the invention.

Example 1

Blood Sampling

Blood is preferably collected by venous puncture using a 20 gauge multi-sample needle and evacuated tubes, although fingertip puncture, plantar surface puncture, earlobe puncture, etc., may suffice for small volumes. For whole blood collection, blood specimens are collected by trained study personnel in EDTA-containing blood collection tubes. For serum collection, blood specimens are collected by trained study personnel in thrombin-containing blood collection tubes. Blood is allowed to clot for 5-10 minutes, and serum is separated from insoluble material by centrifugation. For plasma collection, blood specimens are collected by trained study personnel in citrate-containing blood collection tubes and centrifuged for $\geq 12$ minutes. Samples may be kept at 4° C. until use, or frozen at −20° C. or colder for longer term storage. Whole blood is preferably not frozen.

Example 2

Biochemical Analyses

BNP is measured using standard immunoassay techniques. These techniques involve the use of antibodies to specifically bind the protein targets. An antibody directed against BNP is biotinylated using N-hydroxysuccinimide biotin (NHS-biotin) at a ratio of about 5 NHS-biotin moieties per antibody. The biotinylated antibody is then added to wells of a standard avidin 384 well microtiter plate, and biotinylated antibody not bound to the plate is removed. This formed an anti-BNP solid phase in the microtiter plate. Another anti-BNP antibody is conjugated to alkaline phosphatase using standard techniques, using SMCC and SPDP (Pierce, Rockford, Ill.). The immunoassays are performed on a TECAN Genesis RSP 200/8 Workstation. Test samples (10 μL) are pipeted into the microtiter plate wells, and incubated for 60 min. The sample is then removed and the wells washed with a wash buffer, consisting of 20 mM borate (pH 7.42) containing 150 mM NaCl, 0.1% sodium azide, and 0.02% Tween-20. The alkaline phosphatase-antibody conjugate is then added to the wells and incubated for an additional 60 min, after which time, the antibody conjugate is removed and the wells washed with a wash buffer. A substrate, (AttoPhos®, Promega, Madison, Wis.) is added to the wells, and the rate of formation of the fluorescent product is related to the concentration of the BNP in the test samples.

Example 3

Identification of BNP Peptides in Spiked Test Samples

Purified BNP (either BNP1-108 or BNP77-108) is added to human blood, serum and plasma test samples, and allowed to incubate for from 5 minutes to 24 hours minutes at 22° C. Following this incubation, the samples are subjected to the following analysis to identify BNP-derived peptides present in the samples.

Test samples were analyzed using a chip-based platform (Ciphergen Biosystems ProteinChip®) coated with anti-BNP antibodies (mouse monoclonal or recombinant human antibodies). For preparing the surface, Protein A or Protein G from *Staphylococcus* species or Protein D from *Haemophilus* species is immobilized to an epoxide on a PS2 ProteinChip® surface by incubation for 2 hours in a humid chamber at room temperature. Residual epoxide sites are blocked with 0.5M ethanolamine in phosphate buffered saline (PBS), pH 8.0 for 15 minutes, then the ProteinChip® is washed 1× with 0.5% Triton X-100 in PBS and 3× in PBS for 15 minutes each. The ProteinChip® is air dried. About 2 μL of each desired antibody is applied to individual array locations at 2-3 mg/mL. The chip is incubated in a humid environment for 1-10 hours. The ProteinChip® is washed 1× with 0.5% Triton X-100 in PBS and 3× in PBS for 15 minutes each, air dried, and is ready for use.

The array locations are exposed to sample for from 10 minutes to 24 hours in a humid environment at room temperature. Unbound material is removed by washing in one or more suitable buffers selected to provide a desired level of stringency (that is, removal of material bound at lower affinity, such as nonspecific background binding). Suitable buffers include PBS; PBS containing 0.05% v/v Tween 20; PBS containing 0.1-3M urea; 20 mM borate (pH 7.42) containing 150 mM NaCl, 0.1% sodium azide, and 0.02% Tween-20; and 0.1M urea, 50 mM CHAPS, 150 mM KCl, pH 7-8. This list is not meant to be limiting, and additional buffers can readily be selected for use by those of skill in the art.

SELDI-TOF-MS is used to determine the identity of polypeptides bound to the anti-BNP antibodies by mass analysis. See, e.g., U.S. Pat. Nos. 5,719,060; 5,894,063; 6,020,208; 6,027,942; and 6,124,137, each of which is hereby incorporated in its entirety, including all tables, figures, and claims. Following drying of the surface, a matrix solution is applied (e.g., sinapinic acid). Each array location is subsequently interrogated with a laser desorption/ionization source, and the ions generated analyzed by SELDI-TOF. Peptide ID is obtained by matching an observed m/z to a predicted molecular weight. Additional resolution can be obtained using the MS/MS methods disclosed in U.S. patent application Publication No. US 2002/0182649, which is incorporated by reference herein.

The following BNP fragments were identified in spiked plasma samples: BNP77-106; BNP79-106; BNP79-108; BNP77-108; BNP69-100; BNP76-107; BNP39-86; BNP53-85; BNP66-98; BNP30-103; BNP11-107; and BNP9-106. In addition, methionine oxidation was be observed as a 15-16 Dalton increase from the predicted molecular weight of a given fragment. Significant oxidation of one or two methionines was be observed in those fragments containing methionine residues. Moreover, a "total BNP" measurement obtained by summation of the area under the peaks of observed fragments indicated that not all of the BNP added was being detected by the antibodies used. This leads to the conclusion that BNP fragments are present in these samples.

Example 4

Identification of BNP Peptides in Patient Test Samples

Plasma, serum, or blood samples obtained from seven human patients presenting for clinical evaluation of chest pain are subjected to the same analysis described in Example 3. Initial patient screening is performed by trained medical personnel, and a clinical diagnosis is obtained by conventional medical means. Plasma samples are obtained from each patient at clinical presentation, and an "apparent BNP" concentration measured by immunoassay, using purified BNP as a standard.

A summary of results for 10 patients is provided in the following table:

| Patient | Clinical Diagnosis | Apparent BNP (pg/mL) |
|---------|--------------------|-----------------------|
| 22085 | Unstable angina | 39.6 |
| 22995 | Non-cardiac chest pain | 161 |
| 21231 | Unstable angina | 353.5 |
| 16221 | Acute myocardial infarction | 654.8 |
| 9240 | Congestive heart failure, diastolic dysfunction | 905.5 |
| 9842 | Echo ejection fraction 44%, enlarged left atrium/ventricle | 1588.7 |
| 21221 | Hospitalization for hyperkalemia | 3561.9 |
| 8329 | Class IV Congestive heart failure | 1207.3 |
| 5478 | Ischemic stroke | 2410.6 |
| 10323 | Subarachnoid hemorrhage | 591.9 |

The following BNP fragments were identified in plasma samples from the various samples: BNP3-108; BNP77-108; BNP79-108; BNP80-108; BNP81-108; and BNP83-108. Additional peaks, which have not yet been related to a BNP sequence, are seen at the following molecular weights: about 2576; about 2676; about 2792; about 3154; about 3370 (see FIGS. 7A and B). Additional unidentified polypeptides were also captured by the antibodies.

In addition, a fragment corresponding to the molecular weight of a tetrameric BNP77-108 was also observed in certain samples (m/z about 12,900). While not wishing to be bound to a particular mechanism, thiol-disulfide interchanges have been reported in proteins including acetylcholinesterase. The disulfide exchange reaction originates from nucleophilic attack on a sulfur atom of the disulfide by the free thiol. As BNP77-108 contains cysteine residues that ordinarily participate in intramolecular disulfide bond formation, high concentrations of mature BNP formation can result in formation of multimeric forms by interaction of reduced and oxidized BNP forms.

In addition, variations in the BNP fragments were observed that were diagnosis-dependent. For example, patient 21231 exhibited a high level of observable BNP3-108 and an intermediate "apparent BNP" concentration, while patient 9240 exhibited little BNP3-108 despite a much higher "apparent BNP" concentration. Thus, BNP3-108, either alone or together with a BNP concentration reflective of a number of additional fragments being bound by the antibody may distinguish unstable angina or myocardial infarction from congestive heart failure.

Example 5

Anti-BNP-106.3 (monoclonal), anti-BNP-.5 (Omniclonal) antibodies were supplied by Biosite. The antibodies were diluted to a final concentration of 0.5 mg/ml with 0.1M sodium bicarbonate 0.05% TritonX100 pH 9. Aliquots of 3 µl were added per spot of Reactive Surface (RS) ProteinChip® array (Ciphergen). The coupling was allowed to proceed at 4 C for 16 hr. The chips were blocked with 1M TrisHCl pH 8 and then BSA (1 mg/ml) in 0.5M TrisHCl, 0.1% TritonX100 pH 8. Excess antibodies were washed away with 1% TritonX100 PBS, followed by 10% PEG 0.1% TritonX100 PBS and finally with 0.1% TritonX100 PBS.

Purified BNP (Biosite) was diluted into 50% human serum (Intergen), or 50% human EDTA plasma (Biosite) with/without protease inhibitor cocktail (Roche). Aliquots of 100 µl of each BNP standard were incubated with antibodies immobilized on RS ProteinChip® array in a bioprocessor (Ciphergen). BNP calibrators in plasma (Biosite) were diluted 1:1 and aliquots of 150 µl were incubated separately with antibodies on RS ProteinChip® array. Patient EDTA plasma samples were diluted 1:1 and aliquots of 150 µl were incubated separately with antibodies on RS ProteinChip® array. After 16 hr of incubation at 4 C with shaking, the arrays were washed with 125 µl of 1M urea 0.1% CHAPS 50 mM TrisHCl pH 7.5 two times. After rinsing with water and air dried, 2 µl of sinapinic acid or cyano hydroxycinnamic acid were added per spot. The retained proteins were detected by a PBSII mass spectrometer (Ciphergen). (see FIGS. 2A and B).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

---

We claim:

1. A purified BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106.

2. The purified BNP fragment according to claim 1, wherein one or more methionine residues of the fragment are oxidized.

3. A method of assaying BNP comprising:

capturing one or more BNP polypeptides from a subject sample, thereby providing a purified BNP fragment of claim 1; and specifically measuring a presence or an amount of at least one captured BNP polypeptide selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106.

4. The method of claim 3, further comprising the capture and specific measurement of BNP77-108.

5. The method of claim 3, wherein the one or more BNP polypeptides are from a clinical sample, and the method further comprising correlating the presence or amount of at least one captured BNP polypeptide with a clinical parameter.

6. The method of claim 5, wherein the clinical parameter is a sign or symptom of a disease.

7. The method of claim 5, wherein the sign or symptom of a disease is a cardiovascular disease.

8. The method of claim 5, wherein the disease is selected from the group consisting of stroke, congestive heart failure (CHF), cardiac ischemia, systemic hypertension, and acute myocardial infarction.

9. The method of claim 5, further comprising correlating the presence or amount of the BNP polypeptide to the probability of a future adverse event in the human from which the test sample was obtained.

10. The method of claim 9, wherein the future adverse event is selected from the group consisting of vascular injury caused by cerebral vasospasm, subarrachnoid hemorrhage, death, myocardial infarction and congestive heart failure.

11. The method of claim 5, further comprising specifically measuring at least one biomolecular interactor of BNP or an antibody to a BNP polypeptide and correlating the measurement(s) with the clinical parameter.

12. The method of claim 5, further comprising specifically measuring presence or amount at least one BNP polypeptide selected from the group consisting of BNP1-76, BNP77-108, BNP1-108 and pre-proBNP and correlating the measurement(s) with the clinical parameter.

13. The method of claim 5, wherein the clinical parameter is acute coronary syndrome.

14. The method of claim 5, wherein the correlating correlates the presence or amount of at least one BNP polypeptide selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106.

15. The method of claim 3, wherein at least one BNP polypeptide is captured with an antibody.

16. The method of claim 15, wherein the antibody captures a plurality of BNP polypeptides from the sample.

17. The method of claim 15, wherein the antibody is a monoclonal antibody or a pool of antibodies.

18. The method of claim 3, wherein the capturing step comprises:

providing a SELDI probe comprising an antibody attached to a surface of a support;

contacting the antibody with a sample, whereby the antibody captures the BNP polypeptides from the sample; and the specifically measuring step comprises specifically measuring the presence or amount of the at least one captured BNP polypeptide by SELDI.

19. The method of claim 18, wherein the SELDI is performed using a SELDI biochip with a chromatographic surface.

20. The method of claim 3, wherein the one or more BNP polypeptides is/are captured with a biospecific capture reagent.

21. The method of claim 3, wherein the one or more BNP polypeptides is/are captured with a chromatographic adsorbent.

22. The method of claim 3, further comprising capturing and measuring a polypeptide interactor of at least one of the one or more captured BNP polypeptides.

23. The method of claim 3, wherein the one or more captured BNP polypeptides is/are measured by mass spectrometry.

24. The method of claim 23, wherein the one or more captured BNP polypeptide is/are measured by SELDI.

25. The method of claim 3, wherein the capturing captures a plurality of BNP polypeptides selected from the group and the specifically measuring specifically measures a plurality of BNP polypeptides selected from the group.

26. A method comprising:
(a) capturing BNP polypeptides from a sample, wherein the polypeptides comprise at least one BNP polypeptide selected from a first group consisting of BNP1-76, BNP77-108, BNP1-108 and pre-pro-BNP, and at least one BNP polypeptide selected from a second group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106, thereby providing a purified BNP fragment of claim 1; and
(b) specifically measuring a captured BNP polypeptide from the first group or second group or both.

27. The method of claim 26, wherein the captured BNP polypeptide is from the first group.

28. The method of claim 26, wherein the captured BNP polypeptide is from the second group.

29. The method of claim 26, wherein the specifically measuring step specifically measures an amount of at least one captured BNP polypeptide from the first group and an amount of at least one captured BNP polypeptide selected from the second group.

30. The method of claim 29, further comprising determining relative ratio of the amounts of each specifically measured BNP polypeptide.

31. The method of claim 26, wherein the BNP polypeptides are captured with a biospecific capture reagent.

32. The method of claim 26, wherein the BNP polypeptides are captured with a chromatographic adsorbent.

33. The method of claim 26, further comprising specifically measuring at least one BNP polypeptide selected from the second group.

34. The method of claim 26, further comprising capturing and measuring a polypeptide that interacts with a BNP polypeptide.

35. The method of claim 26, wherein the specifically measuring step is performed by mass spectrometry.

36. The method of claim 26, wherein the specifically measuring step is performed by affinity mass spectrometry.

37. The method of claim 26, wherein the sample is a subject sample and the method further comprises:
correlating the specifically measured BNP polypeptide with a clinical parameter in the subject.

38. The method of claim 26, wherein the clinical parameter is presence or absence of acute coronary syndrome.

39. A method for discovering polypeptides that interact with a BNP fragment, comprising:
(a) capturing a BNP fragment selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108, and BNP79-106 with a biospecific capture reagent, thereby providing a purified BNP fragment of claim 1;
(b) removing molecules that are not bound to the biospecific capture reagent or BNP fragment; and
(c) measuring molecules bound to the captured BNP fragment.

40. The method of claim 39, wherein the molecules are measured by SELDI.

41. A method for qualifying an immunoassay calibrator for a BNP immunoassay comprising:
(a) providing an immunoassay calibrator for a BNP immunoassay, wherein the calibrator comprises a designated concentration of one or more BNP polypeptides;
(b) capturing polypeptides from the calibrator with an antibody to a BNP polypeptide, thereby providing a purified BNP fragment of claim 1; and
(c) specifically measuring an amount of at least one polypeptide selected from the group consisting of BNP79-108, BNP77-106, BNP39-86, BNP53-85, BNP66-98, BNP30-106, BNP11-107, BNP9-106, BNP69-100, BNP76-107, BNP69-108, BNP80-108, BNP81-108, BNP83-108, BNP30-103, BNP3-108 and BNP79-106 whereby the measured amount provides an indication of the quality of the immunoassay calibrator.

42. The method of claim 41, further comprising specifically measuring at least one BNP polypeptide selected from the group consisting of BNP1-76, BNP77-108, BNP1-108, and pre-proBNP.

43. The method of claim 42, further comprising determining the amount of the at least one BNP polypeptide selected from the group consisting of BNP1-76, BNP77-108, BNP1-108, and pre-proBNP as a function of total polypeptide captured by the antibody.

44. The method of claim 41, wherein the antibody is an antibody used with the immunoassay calibrator in a commercial immunoassay.

45. The method of claim 41, wherein the amount is measured by SELDI.

* * * * *

SEQUENCE LISTING

<160> NUMBER OF SEQ ID NOS: 5

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
 1               5                  10                  15

Leu Gln Glu Gln Arg Asn His Leu Gln Gly Lys Leu Ser Glu Leu Gln
                20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
        50                  55                  60

Arg Lys Met Val Leu Tyr Thr Leu Arg Ala Pro Arg Ser Pro Lys Met
 65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 2
<211> LENGTH: 134
<212> TYPE: PRT
<213> ORGANISM: Homo sapiens

<400> SEQUENCE: 2

Met Asp Pro Gln Thr Ala Pro Ser Arg Ala Leu Leu Leu Leu Leu Phe
 1               5                  10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
        50                  55                  60

Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130

<210> SEQ ID NO 3
<211> LENGTH: 126
<212> TYPE: PRT
<213> ORGANISM: Homo sapiens

<400> SEQUENCE: 3

```
Asn Pro Met Tyr Asn Ala Val Ser Asn Ala Asp Leu Met Asp Phe Lys
 1               5                  10                  15

Asn Leu Leu Asp His Leu Glu Glu Lys Met Pro Leu Glu Asp Glu Val
             20                  25                  30

Val Pro Pro Gln Val Leu Ser Asp Pro Asn Glu Glu Ala Gly Ala Ala
         35                  40                  45

Leu Ser Pro Leu Pro Glu Val Pro Pro Trp Thr Gly Glu Val Ser Pro
     50                  55                  60

Ala Gln Arg Asp Gly Gly Ala Leu Gly Arg Gly Pro Trp Asp Ser Ser
 65                  70                  75                  80

Asp Arg Ser Ala Leu Leu Lys Ser Lys Leu Arg Ala Leu Leu Thr Ala
             85                  90                  95

Pro Arg Ser Leu Arg Arg Ser Ser Cys Phe Gly Gly Arg Met Asp Arg
        100                 105                 110

Ile Gly Ala Gln Ser Gly Leu Gly Cys Asn Ser Phe Arg Tyr
        115                 120                 125

<210> SEQ ID NO 4
<211> LENGTH: 151
<212> TYPE: PRT
<213> ORGANISM: Homo sapiens

<400> SEQUENCE: 4

Met Ser Ser Phe Ser Thr Thr Thr Val Ser Phe Leu Leu Leu Leu Ala
 1               5                  10                  15

Phe Gln Leu Leu Gly Gln Thr Arg Ala Asn Pro Met Tyr Asn Ala Val
             20                  25                  30

Ser Asn Ala Asp Leu Met Asp Phe Lys Asn Leu Leu Asp His Leu Glu
         35                  40                  45

Glu Lys Met Pro Leu Glu Asp Glu Val Val Pro Pro Gln Val Leu Ser
     50                  55                  60

Asp Pro Asn Glu Glu Ala Gly Ala Ala Leu Ser Pro Leu Pro Glu Val
 65                  70                  75                  80

Pro Pro Trp Thr Gly Glu Val Ser Pro Ala Gln Arg Asp Gly Gly Ala
             85                  90                  95

Leu Gly Arg Gly Pro Trp Asp Ser Ser Asp Arg Ser Ala Leu Leu Lys
        100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
        130                 135                 140

Gly Cys Asn Ser Phe Arg Tyr
145                 150

<210> SEQ ID NO 5
<211> LENGTH: 126
<212> TYPE: PRT
<213> ORGANISM: Homo sapiens

<400> SEQUENCE: 5

Met His Leu Ser Gln Leu Leu Ala Cys Ala Leu Leu Leu Thr Leu Leu
 1               5                  10                  15

Ser Leu Arg Pro Ser Glu Ala Lys Pro Gly Ala Pro Pro Lys Val Pro
             20                  25                  30

Arg Thr Pro Pro Ala Glu Glu Leu Ala Glu Pro Gln Ala Ala Gly Gly
         35                  40                  45
```

```
Gly Gln Lys Lys Gly Asp Lys Ala Pro Gly Gly Gly Ala Asn Leu
        50              55              60

Lys Gly Asp Arg Ser Arg Leu Leu Arg Asp Leu Arg Val Asp Thr Lys
65              70              75                      80

Ser Arg Ala Ala Trp Ala Arg Leu Leu Gln Glu His Pro Asn Ala Arg
                85              90              95

Lys Tyr Lys Gly Ala Asn Lys Lys Gly Leu Ser Lys Gly Cys Phe Gly
            100             105             110

Leu Lys Leu Asp Arg Ile Gly Ser Met Ser Gly Leu Gly Cys
        115             120             125
```